US011295863B2

(12) United States Patent
Perentesis et al.

(10) Patent No.: US 11,295,863 B2
(45) Date of Patent: Apr. 5, 2022

(54) PREDICTIVE CLINICAL ASSAYS AND METHODS OF USING SAME

(71) Applicant: Children's Hospital Medical Center, Cincinnati, OH (US)

(72) Inventors: John Perentesis, Cincinnati, OH (US); Bruce Aronow, Cincinnati, OH (US); Rebekah Karns, Cincinnati, OH (US); Mayur Sarangdhar, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 273 days.

(21) Appl. No.: 16/094,600

(22) PCT Filed: May 2, 2017

(86) PCT No.: PCT/US2017/030540
§ 371 (c)(1),
(2) Date: Oct. 18, 2018

(87) PCT Pub. No.: WO2017/192511
PCT Pub. Date: Nov. 9, 2017

(65) Prior Publication Data
US 2019/0112669 A1    Apr. 18, 2019

Related U.S. Application Data

(60) Provisional application No. 62/330,319, filed on May 2, 2016.

(51) Int. Cl.
| | |
|---|---|
| *G16H 50/30* | (2018.01) |
| *A61B 5/00* | (2006.01) |
| *A61P 35/00* | (2006.01) |
| *A61K 31/475* | (2006.01) |
| *A61K 31/573* | (2006.01) |
| *A61K 31/655* | (2006.01) |
| *A61K 31/675* | (2006.01) |
| *A61K 31/704* | (2006.01) |
| *A61K 31/7048* | (2006.01) |
| *A61K 38/14* | (2006.01) |

(52) U.S. Cl.
CPC ........... *G16H 50/30* (2018.01); *A61B 5/4848* (2013.01); *A61K 31/475* (2013.01); *A61K 31/573* (2013.01); *A61K 31/655* (2013.01); *A61K 31/675* (2013.01); *A61K 31/704* (2013.01); *A61K 31/7048* (2013.01); *A61K 38/14* (2013.01); *A61P 35/00* (2018.01); *C12Q 2600/106* (2013.01); *C12Q 2600/156* (2013.01); *G01N 2800/52* (2013.01)

(58) Field of Classification Search
CPC .......... G01N 2800/52; C12Q 2600/156; C12Q 2600/106; G16H 50/30; A61B 5/4848
See application file for complete search history.

(56) References Cited

U.S. PATENT DOCUMENTS

| | | | |
|---|---|---|---|
| 2001/0034023 A1 | 10/2001 | Stanton et al. | |
| 2012/0014956 A1 | 1/2012 | Kupper et al. | |
| 2017/0101678 A1* | 4/2017 | Hu | ........................ C12Q 1/6883 |

FOREIGN PATENT DOCUMENTS

WO    WO 2015/109608 A1    7/2015

OTHER PUBLICATIONS

Reference SNP report for rs5305. https://www.ncbi.nlm.nih.gov/snp/rs5305, accessed Nov. 27, 2020, pp. 1-7 (Year: 2020).*
Jou et al. ICSH review of the measurement of the erythrocte sedimentation rate. Int. Jnl. Lab. Hem. 2011, vol. 33, pp. 125-132 (Year: 2011).*
Cahkoglu, M., et al., "The Association Between Polymorphic Genotypes of Glutathione S-Transferases and COPD in the Turkish Population," Biochemical Genetics, 2006, 44(7/8):307-319, 13 pgs.
Froudarakis, M., et al., "Revisiting bleomycin from pathophysiology to safe clinical use," Critical Reviews in Oncology/Hematology. 2013, 87:90-100, 11 pgs.
Nagase, T., et al., "A pivotal role of cytosolic phospholipase A2 in bleomycin-induced pulmonary fibrosis," Nature Medicine, 2002, 8(5):480-484, 5 pgs.
Nieuweboer, A.J.M., et al., "Role of genetic variation in docetaxel-induced neutropenia and pharmacokinetics," The Pharmacogenomics Journal, 2016, 16:519-524, 6 pgs.
Paun, A., et al., "Association Analysis Reveals Genetic Variation Altering Bleomycin-Induced Pulmonary Fibrosis in Mice," Am J Respir Cell Mol Biol, 2013, 48(3):330-336, 7 pgs.
Van Der Schoot, G.G.F., et al., "Variation in the HFE gene is associated with the development of bleomycin-induced pulmonary toxicity in testicular cancer patients," European Journal of Cancer, 2016, 59:134-141, 8 pgs.
European Search Report, Supplementary, and Written Opinion dated Dec. 16, 2019 for Application No. EP 17793107.8, 11 pgs.
Aleman, B.M.P., et al. "Long-Term Cause-Specific Mortality of Patients Treated for Hodgkin's Disease," J Clin Oncol, 2003, 21: 3431-3439, 9 pgs.
American Cancer Society, "Cancer Facts and Figures 2015," American Cancer Society Inc., Atlanta, GA, USA, 2015, 56 pgs.
Carver, J.R., et al., "American Society of Clinical Oncology Clinical Evidence Review on the Ongoing Care of Adult Cancer Survivors: Cardiac and Pulmonary Late Effects," Journal of Clinical Oncology: Official Journal of the American Society of Clinical Oncology, Sep. 2007; 25(25):3991-4008, 18 pgs.

(Continued)

*Primary Examiner* — Olivia M. Wise
(74) *Attorney, Agent, or Firm* — Frost Brown Todd LLC; Nicole M. Tepe

(57) ABSTRACT

Disclosed are methods of treating an individual at risk for a negative outcome associated with a treatment for a disease, in particular a proliferative disorder such as cancer. The method may include the steps of creating a predictive assay that includes both a biomarker and a genetic mutation. The predictive assay indicates the likelihood of a negative outcome associated with a particular treatment in a particular individual, such that an individual may be administered a treatment less likely to be associated with a negative outcome.

19 Claims, 11 Drawing Sheets

(56) References Cited

OTHER PUBLICATIONS

Castellino, S.M., et al., "Morbidity and mortality in long-term survivors of Hodgkin lymphoma: a report from the Childhood Cancer Survivor Study," Blood, Feb. 2011, 117(6):1806-16, 11 pgs.
Cho, W.C.S., et al., "MiR-145 inhibits cell proliferation of human lung adenocarcinoma by targeting EGFR and NUDT1," RNA Biology, 2011, 8(1): 125-31, 7 pgs.
Crawford, M, et al., "MicroRNA 133B targets pro-survival molecules MCL-1 and BCL2L2 in lung cancer," Biochemical and Biophysical Research Communications, 2009, 388(3):483-9, 7 pgs.
Diefenbach, C.S., et al., "Hodgkin Lymphoma: Current Status and Clinical Trial Recommendations," JNCIJ Natl Cancer Inst, 2017, 109(4):djw249, 12 pgs.
Friedman, D.L., et al., "Dose-Intensive Response-Based Chemotherapy and Radiation Therapy for Children and Adolescents with newly Diagnosed Intermediate-Risk Hodgkin Lymphoma: A Report from the Children's Oncology Group Study AHOD0031," Journal of Clinical Oncology, 2014, 32(32):3651-8, 8 pgs.
Friedman, D.L., et al., "Late Effects of Treatment for Hodgkin Lymphoma," Journal of the National Comprehensive Cancer Network: JNCCN 2006; 4(3):249-57, 9 pgs.
García-Closas, M., et al., "NAT2 slow acetylation, GSTM1 null genotype, and risk of bladder cancer: results from the Spanish Bladder Cancer Study and meta-analyses," Lancet, 2005, 366(9486):649-59, 11 pgs.
Gonzalez, C.A., et al., "Genetic Susceptibility and Gastric Cancer Risk," International Journal of Cancer, 2002, 100(3):249-60, 12 pgs.
Guo, J., et al., "MicroRNA-217 Functions as a Tumour Suppressor Gene and Correlates with Cell Resistance to Cisplatin in Lung Cancer," Molecules and Cells, 2014, 37(9):664-71, 8 pgs.
Gupta, V.H., et al., "Association of N-acetyltransferase 2 and cytochrome P450 2E1 gene polymorphisms with antituberculosis drug-induced hepatotoxicity in Western India," Journal of Gastroenterology and Hepatology, 2013, 28(8): 1368-74, 7 pgs.
Hartkoorn, R.C., et al., "HIV protease inhibitors are substrates for OATP1A2, OATP1B1 and OATP1B3 and lopinavir plasma concentrations are influenced by SLCOIB1 polymorphisms," Pharmacogenetics and Genomics, 2010, 20(2): 112-20, 19 pgs.
Higa, G.M., et al., "Elevation of the Erythrocyte Sedimentation Rate Precedes Exacerbation of Bleomycin-Induced Pulmonary Toxicity: Report of Two Cases and Review of Literature," Pharmacotherapy, 1997, 17(6): 1315-21, 7 pgs.
Ieiri, I., et al., "Genetic polymorphisms of uptake (OATP1B1, 1B3) and efflux (MRP2, BCRP) transporters: implications for interindividual differences in the pharmacokinetics and pharmacodynamics of statins and other clinically relevant drugs," Expert opinion on Drug Metabolism & Toxicology, 2009, 5(7):703-29, 27 pgs.
Karns, R., et al., "Pharmacogenomic prediction of treatment-induced severe lung toxicity in Hodgkin lymphoma (HL)," Journal of Clinical Oncology, May 18, 2016, 34(15 Supp):7522, downloaded from: http://ascopubs.org/doi/abs/10.1200/JCO.2016.34.15_suppl.7522, Abstract only, 4 pgs.
König, S.K., et al., "Impact of drug transporters on cellular resistance towards saquinavir and darunavir," The Journal of Antimicrobial Chemotherapy, 2010, 65(11):2319-28, 10 pgs.
Kung, F.H., et al., "POG 8625: A Randomized Trial Comparing Chemotherapy with Chemoradiotherapy for Children and Adolescents with Stages I, IIA, IIIA₁ Hodgkin Disease: A Report from the Children's Oncology Group," Journal of Pediatric Hematology/Oncology, 2006, 28(6):362-8, 7 pgs.
Létourneau, I.J., et al., "Functional characterization of non-synonymous single nucleotide polymorphisms in the gene encoding human multidrug resistance protein 1 (MRP1/ABCC1)," Pharmacogenetics and Genomics, 2005, 15(9):647-57, 11 pgs.
Liang, A., et al., "Loss of glutathione S-transferase A4 accelerates obstruction-induced tubule damage and renal fibrosis," The Journal of Pathology, 2012, 228(4):448-58, 11 pgs.

Lino Cardenas, C.L., et al., "miR-199a-5p Is Upregulated during Fibrogenic Response to Tissue Injury and Mediates TGFbeta-Induced Lung Fibroblast Activation by Targeting Caveolin-1," PLoS Genetics, 2013, 9(2):e1003291, 24 pgs.
Martin, W.G., et al., "Bleomycin Pulmonary Toxicity Has a Negative Impact on the Outcome of Patients with Hodgkin's Lymphoma," Journal of Clinical Oncology, 2005, 23(30):7614-20, 7 pgs.
Mauz-Körholz, C. et al., "Procarbazine-Free OEPA-COPDAC Chemotherapy in Boys and Standard OPPA-COPP in Girls Have Comparable Effectiveness in Pediatric Hodgkin's Lymphoma: The GPHH-HD-2002 Study," Journal of Clinical Oncology, Aug. 2010, 28(23):3680-3686, 7 pgs.
Mertens, A.C., et al., "Pulmonary complications in Survivors of Childhood and Adolescent Cancer. A Report from the Childhood Cancer Survivor Study," Cancer, 2002, 95(11):2431-41, 11 pgs.
Mullis, K.B., et al., "Specific Synthesis of DNA in Vitro via a Polymerase-Catalyzed Chain Reaction," Chapter [21], in Methods In Enzymology, 1987, 155:335-50.
National Institute of Science and Technology (NIST), "Log Odds Ratio," Statistical Engineering Division Dataplot, Nov. 16, 2015, downloaded from: https://www.itl.nist.gov/div898/software/dataplot/refman2/auxillar/logoddra.htm, 4 pgs.
Perentesis, MD Faap, J., "When Research is Currency: Leveraging Research to Develop a Program," Presented at Texas AYA, Feb. 26, 2016, downloaded from: http://ce.unthsc.edu/assets/1787/PERENTESIS%20A%202016%20Texas%20AYA%20Conference%2026FEB2016e1.pdf, 47 pgs.
Provost, P.R., et al., "Genes Involved in the Adrenal Pathway of Glucocorticoid Synthesis Are Transiently Expressed in the Developing Lung," Endocrinology, 2005, 146(5):2239-45, 7 pgs.
Schwartz, C.L., et al., "A risk-adapted, response-based approach using ABVE-PC for children and adolescents with intermediate- and high-risk Hodgkin lymphoma: the results of P9425," Blood, 2009, 114(10):2051-9, 10 pgs.
Straus, D.J., "Long-Term survivorship at a price: late-term, therapy-associated toxicities in the adult Hodgkin lymphoma patient," Therapeutic Advances in Hematology, 2011, 2(2): 111-119, 9 pgs.
Tang, D., et al., "Identification of plasma microRNAs as novel noninvasive biomarkers for early detection of lung cancer," European Journal of Cancer Prevention, 2013, 22(6):540-8, 9 pgs.
Wang, H., et al., "Genetic Susceptibility of Lung Cancer Associated With Common Variants in the 3' Untranslated Regions of the Adenosine Triphosphate-Binding Cassette B1 (ABCB1) and ABCCI Candidate Transporter Genes for Carcinogen Export," Cancer, 2009, 115(3):595-607, 13 pgs.
Wilson, J.F., et al., "Population genetic structure of variable drug response," Nature Genetics, 2001, 29(3):265-69, 5 pgs.
Wolden, S.L., et al., "Long-term Results of CCG 5942: A Randomized Comparison of Chemotherapy With and Without Radiotherapy for Children With Hodgkin's Lymphoma—A Report From the Children's Oncology Group," Journal of Clinical Oncology, 2012, 30(26):3174-80, 7 pgs.
Xiong, S., et al., "MicroRNA-7 Inhibits the Growth of Human Non-Small Cell Lung Cancer A549 Cells through Targeting BCL-2," International Journal of Biological Sciences, 2011, 7(6):805-14, 10 pgs.
Xu, M., et al., "miR-133a suppresses cell proliferation, migration and invasion in human lung cancer by targeting MMP-14," Oncology Reports, 2013, 30(3): 1398-404, 7 pgs.
Yang, S., et al., "miR-145 regulates myofibroblast differentiation and lung fibrosis," FASEB Journal, 2013, 27(6):2382-91, 10 pgs.
Zhang, L., et al., "SHP-1 Deficient Mast Cells Are Hyperresponsive to Stimulation and Critical in Initiating Allergic Inflammation in the Lung," The Journal of Immunology, 2010, 184(3):1180-90 11 pgs.
International Search Report and Written Opinion dated Oct. 3, 2017 for Application No. PCT/US2017/030540, 15 pgs.
U.S. Appl. No. 62/330,319, filed May 2, 2016.

\* cited by examiner

PREDICTIVE CLINICAL ASSAYS AND METHODS OF USING SAME

CROSS REFERENCE TO RELATED APPLICATIONS

This application claims the benefit of and priority to International Application No. PCT/US2017/030540, entitled "Predictive Clinical Assays and Methods of Using Same," filed May 2, 2017, which claims the benefit of and priority to US 62/330,319, of same title to Perentesis et al., filed May 2, 2016, in their entirety and for all purposes.

BACKGROUND

Long-term survival rates in pediatric Hodgkin lymphoma (HL) have risen above 90%,[1] highlighting a priority for the development of treatment regimens ensuring long-term survivor health. Acute and late-onset chemotherapeutic toxicities, some of which become evident only years after chemotherapy and radiation therapies, have become central considerations in the care-decision processes in pediatric cancer patients.[2, 3] Notably, Hodgkin survivors experience significantly increased death rates from lung fibrosis that arises due to damage from chemotherapeutic agents, particularly bleomycin, and radiotherapy (IFRT).[4, 5] Although the risk for severe pulmonary toxicity is low (<5% incidence), it often results in substantial morbidity and mortality that often are only evident years after treatment.[3] In the most severe cases the pathogenic progression of chronic pulmonary toxicity results in fatal complications. The prediction of severe lung toxicity is similarly likely to be relevant to other common cancers that employ bleomycin as a core component of chemotherapy. For example, these include Non-Hodgkin lymphoma, penile cancer, squamous cell carcinoma of the head and neck, squamous cell carcinoma of the vulva, testicular cancer, ovarian and cervical cancer. In any proliferative disorder or cancer in which bleomycin is used alone or with other drugs, the risk of lung toxicity exists.

Given the severity of pulmonary sequelae, treatment personalization for individuals at high risk for lung toxicities should be a priority in Hodgkin lymphoma management, as well as management of many other common cancers that employ bleomycin (such as those listed above). The contemporary approach to mitigate risk for lung complications is to employ serial testing of lung function studies, including the diffusion capacity of carbon monoxide (DLCO), and to eliminate or reduce dosing of bleomycin if abnormal lung function is observed. However, this approach is unsatisfactory because bleomycin dosing is adjusted only after lung toxicity has been incurred. Meaningful integration of demographic, clinical, and genetic characteristics can facilitate the pre-emptive individualization of chemotherapeutic and radiation treatments, and identify the subset of patients at risk for specific complication so that alternative effective therapies can be employed.[6, 7] Patient-specific platform selection and dosing may be used to reduce acute side effects and late toxicities while maximizing cure.

Chemotherapy-induced pulmonary toxicities in Hodgkin lymphoma (HL) patients result in substantial morbidity and mortality, often evident years post-therapy. In fact, the leading overall cause of death from HL is not the malignancy, but is from late complications of therapy. (See, e.g., Aleman B. M., Van Den Belt-Dusebout A. W., Klokman W. J., Van't Veer M. B., Bartelink H., Van Leeuwen F. E. (2003) Long-term cause-specific mortality of patients treated for Hodgkin's disease. J Clin Oncol 21: 3431-3439, Straus D J. Long-Term Survivorship at a Price: Late-Term, Therapy-Associated Toxicities in the Adult Hodgkin Lymphoma Patient. Therapeutic Advances in Hematology. 2011; 2(2): 111-119, Castellino S M, Geiger A M, Mertens A C, Leisenring W M, Tooze J A, Goodman P, Stovall M, Robison L L, Hudson M M. Morbidity and mortality in long-term survivors of Hodgkin lymphoma: a report from the Childhood Cancer Survivor Study. Blood. 2011 Feb. 10; 117(6):1806-16.) Though the most commonly used pediatric and adult standard of care therapy regimens for HL in North America all employ bleomycin, the German Society of Pediatric Oncology and Euronet consortium have successfully developed regimens with comparable efficacy that do not contain bleomycin (e.g. vincristine (Oncovin), etoposide, prednisone, doxorubicin (Adriamycin), or "OEPA" for low risk and OEPA with cyclophosphamide, vincristine, prednisone, dacarbazine (Dac), or "COPDac" for intermediate- and high-risk groups). (See, e.g., Diefenbach C S, Connors J M, Friedberg J W et al. Hodgkin Lymphoma: Current Status and Clinical Trial Recommendations. JNCI J Natl Cancer Inst (2017) 109(4): djw249). Identification of the subset of individuals who are at high-risk for pulmonary complications and associated risk-guided treatment personalization (e.g. selection of standard of care regimens that do not include bleomycin) is an disease management priority for those in need of this treatment.

BRIEF SUMMARY

Disclosed are methods of treating an individual at risk for a negative outcome associated with a treatment for a disease, in particular, a cancer. The method may include the steps of creating a predictive assay that includes both a biomarker and a genetic mutation. The predictive assay indicates the likelihood of a negative outcome associated with a particular treatment in a particular individual, such that an individual may be administered a treatment less likely to be associated with a negative outcome.

DETAILED DESCRIPTION OF THE INVENTION

Definitions

Figure 1:
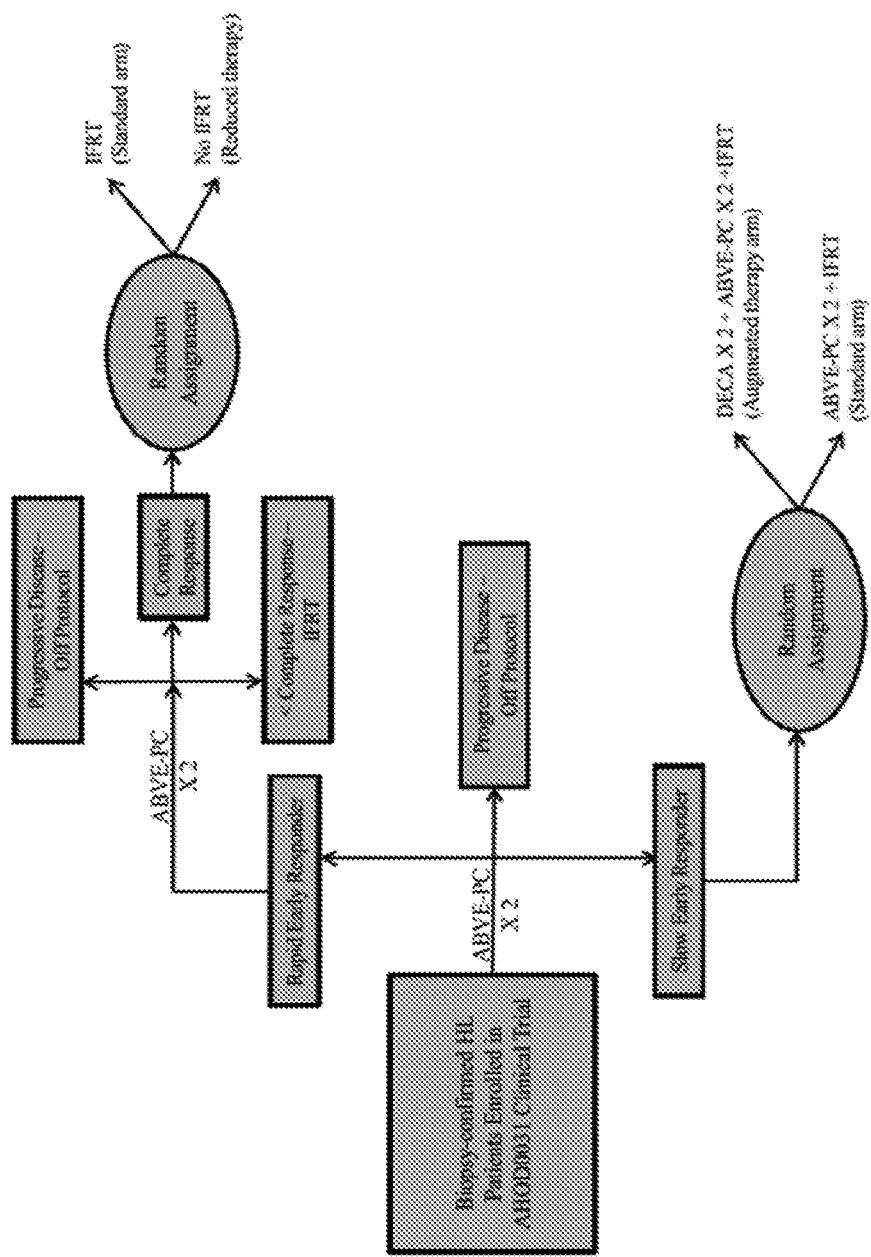
FIG. 1. Diagram of treatment schema. ABVE-PC, doxorubicin, bleomycin, vincristine, etoposide, cyclophosphamide, and prednisone; DECA, dexamethasone, etoposide, cisplatin, and cytarabine; IFRT, radiotherapy.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise.

As used herein, a detectable probe means a probe labeled with a detectable marker, such as, for example, a radioisotope, fluorescent compound, bioluminescent compound, chemiluminescent compound, metal chelator, or enzyme, and which is typically used with PCR methods. Such probes and primers can be used to detect the presence of SNP in a sample.

As used herein, the term "primer" refers to an oligonucleotide used to prime nucleic acid synthesis. A primer hybridizes to the template through complementary base pairing and is therefore used to initiate the replication. Hybridization occurs in the same manner as that described for probes, above. In PCR, two primers are generally used: at least one "forward primer" that typically hybridizes to the sense strand and at least one "reverse primer" that typically hybridizes to the antisense strand.

As used herein, the term "PCR" refers to a technique for exponential amplification of short DNA sequences (usually 50 to 600 bases) within a longer double stranded DNA molecule by enzymatic replication of DNA without using a living organism (Mullis et al. Methods Enzymol. 1987; 155:335-50). Other in vitro amplification technologies can be used to implement the disclosed methods and are well known to those of skill. These methods include, for example, Ligase Chain Reaction (LCR), Nucleic Acids Sequence Based Amplification (NASBA), Strand Displacement Amplification (SDA), Transcription Mediated Amplification (TMA), Branched DNA technology (bDNA) and Rolling Circle Amplification Technology (RCAT).

As used herein, the term "sample" is used in its broadest sense, and refers to any type of material of biological origin, which can be, for example, any fluid, tissue, or cell. For example, a sample can be a biological fluid, e.g., urine, blood, serum, semen, plasma, nasal secretion, cerebrospinal fluid, saliva, etc. Alternatively, a sample can be cultured cells or tissues, cultures of microorganisms, or any fraction or products produced from or derived from biological materials. Optionally, a sample can be purified, partially purified, unpurified, enriched or amplified.

A method of treating an individual having a proliferative disorder, in particular cancer, for example Non-Hodgkin lymphoma, penile cancer, squamous cell carcinoma of the head and neck, squamous cell carcinoma of the vulva, testicular cancer, ovarian or cervical cancer, is disclosed. The method may comprise the steps of identifying a polymorphism in one or more genes selected from NAT2, SLCO1B1, ABCC1, GSTA4, CYP11B1, SLC7A8, and SLCO3A1, in a biological sample of the individual, and measuring an erythrocyte sedimentation rate (ESR) of the individual. In one aspect, wherein at least one or more polymorphism is identified and/or an increased erythrocyte sedimentation rate is observed, the individual is characterized as high risk, and may be administered a protocol that does not include the use of bleomycin. In one aspect, the individual has a number of polymorphisms and/or an erythrocyte sedimentation rate that does not characterize the individual as having an increased risk of lung toxicity, and the individual is treated with bleomycin.

In one aspect, the polymorphism may be a single nucleotide polymorphism selected from rs1799930 in NAT2, rs1041983 in NAT2, rs2291075 in SLCO1B1, rs212091 in ABCC1, rs13197674 in GSTA4, rs4149015 in GSTA4, rs4736312 in CYP11B1, rs5305 in CYP11B2, rs2268873 in SLC7A8, rs1517618 in SLCO3A1, or a combination thereof.

In one aspect, the identification step may comprise identifying a first allelic risk score based on identification of a polymorphism in NAT2, SLCO3A1, and ABCC1.

In one aspect, the polymorphism in NAT2, SLCO3A1, and ABCC1 may be used to generate an allelic risk score ranging from 0 to 5. An erythrocyte sedimentation rate (ESR) may be used to calculate a log-odds score, wherein a sedimentation rate increase of 10 mm/Hg increases a log-odds score by 1.15.

In one aspect, where the individual is identified as high risk for lung toxicity, the individual is administered a protocol that does not contain bleomycin. In this aspect, the protocol that does not include the use of bleomycin may be, for example, vincristine (Oncovin), etoposide, prednisone, doxorubicin (Adriamycin) ("OEPA"). In one aspect, the protocol that does not include the use of bleomycin may be cyclophosphamide, vincristine, prednisone, dacarbazine (Dac), ("COPDac").

In one aspect, the individual is characterized as having a high risk for lung toxicity if a log-odds score of $\geq -3$ for said individual is determined. Alternatively, an individual is characterized as having a low risk for lung toxicity if a log-odds score of $< -3$ for the individual is determined.

Any suitable biological sample may be used to allow for measurement and/or detection of ESR and/or one or more polymorphisms, respectively. In one aspect, the biological sample is any biological fluid containing DNA. The biological sample may be, for example, selected from a tissue, a cell, blood, saliva, or a combination thereof.

The methods may employ a primer complementary to any of the aforementioned polymorphisms. For example, the identification step may be carried out using at least two primers complementary to at least two polymorphisms, or at least three primers complementary to at least three polymorphisms, or at least four primers complementary to at least four polymorphisms, or at least five primers complementary to at least five polymorphisms, or at least six primers complementary to at least six polymorphisms, or at least seven primers complementary to at least seven polymorphisms, or at least eight primers complementary to at least eight polymorphisms, or at least nine primers complementary to at least nine polymorphisms, or ten primers complementary to ten polymorphisms. For the sake of clarity, the polymorphisms referenced in this paragraph are the single nucleotide polymorphisms listed above.

The methods may employ at least two detectable probes complementary to at least two polymorphisms, or at least three detectable probes complementary to at least three polymorphisms, or at least four detectable probes complementary to at least four polymorphisms, or at least five detectable probes complementary to at least five polymorphisms, or at least six detectable probes complementary to at least six polymorphisms, or at least seven detectable probes complementary to at least seven polymorphisms, or at least eight detectable probes complementary to at least eight polymorphisms, or at least nine detectable probes complementary to at least nine polymorphisms, or ten detectable probes complementary to ten polymorphisms. For the sake of clarity, the polymorphisms referenced in this paragraph are the single nucleotide polymorphisms listed above.

In one aspect, a kit for predicting the odds of lung toxicity in a patient having a cancer in response to bleomycin is disclosed. The kit may comprise a means for determining the presence of one or more polymorphisms as described herein, and instructions for recommended treatment of the patient based on the presence of the polymorphisms and an ESR. The kit may contain any of the primers or detectable probes as set forth above.

Applicant conducted a nested case-control study within the Children's Oncology Group Intermediate Risk Hodgkin Lymphoma Clinical Trial, "COG-AHOD0031", assessing associations between severe lung toxicity (primary outcome) and clinical, demographic, and genetic predictors. Variant allele frequencies in drug metabolism enzyme and transporter genes were compared between patients with no/mild (n=929) and severe (n=24) pulmonary toxicities. Significant polymorphisms (p<0.005) were combined into per-individual allelic risk scores by summing risk alleles, and included in a predictive regression model with significant covariates.

Applicant found significant association between severe lung toxicity and single nucleotide polymorphisms in three genes; NAT2, SLCO3A1, and ABCC1. Risk alleles were summed across the three polymorphisms, generating an allelic risk score ranging from 0 to 5. Applicant generated a regression model for the prediction of severe lung toxicity that included allelic risk score and erythrocyte sedimentation rate. Each additional risk allele increased the odds for severe lung toxicity by 2.48 (p<0.0001); each sedimentation rate increase of 10 mm/Hg increased odds by 1.15 (p=0.01). Individuals with a model-generated log-odds score ≥−3 were deemed high-risk; <−3 was low-risk. Within the high-risk group severe lung toxicity prevalence was >9%, within low-risk individuals the prevalence was 1.5%. A second-stage test of two polymorphisms in GSTA4 and SLCO1B1 within the high-risk subset revealed a genetic subset of individuals with a prevalence of >28%. Polymorphisms in CYP11B1, SLC7A8, and SLCO1B1 identified individuals at increased risk at a prevalence of >8% in the low-risk subset.

Net, Applicant has developed two-step process combining risk alleles across eight polymorphisms in seven genes, integrated with erythrocyte sedimentation rate identifies pediatric Hodgkin patients at low (1.0%) and high (>28%) risk for severe pulmonary toxicities.

The Children's Oncology Group (COG) AHOD0031 Intermediate Risk Hodgkin Lymphoma Clinical Trial incorporated a large pediatric Hodgkin cohort with uniform staging and therapy, with consistent and reliable data capture.[7] Extensive clinical and demographic information was gathered on all patients, who were also genotyped for single nucleotide polymorphisms (SNPs) in well-known drug metabolism enzyme and transporter genes. Additionally, acute toxicities (which often correlate with late toxicities)[3] were recorded longitudinally throughout therapy. A nested case-control study within the cohort represents a unique opportunity to identify baseline clinical/demographic and genetic predictors associated with pulmonary toxicities. Integration of these predictors into a predictive clinical model would potentially permit prospective, patient-specific precision drug platform selection. Since multiple, equally effective treatment regimens are available for the treatment of Hodgkin lymphoma, individuals at high risk for pulmonary toxicities could be treated on regimens that do not include drugs that mediate lung toxicity.[6, 8]

Applicant has generated a predictive model of severe acute pulmonary toxicity based on patient clinical characteristics and genotypes of several well-known SNPs in drug metabolism/transport genes.

Through this model, high-risk patients may be identified and appropriately treated with an alternate effective therapy that does not contain bleomycin, and is less likely to induce pulmonary damage.

EXAMPLES

Methods
Patients:

The COG National Hodgkin Lymphoma Study AHOD0031 cohort has been previously described.[9] Briefly, patients aged <22 years at diagnosis with biopsy-proven Hodgkin Lymphoma were recruited between 2002 and 2009 across >200 study locations (n=1712 patients), as approved by the National Cancer Institute and participating institutional review boards. Staging, B symptoms, and bulk disease were reported. All patients received four cycles of ABVE-PC (Adriamycin, Bleomycin, Vincristine, Etoposide, Prednisone, and Cyclophosphamide; FIG. 1). Depending on response (slow or rapid early response), patients subsequently were randomized to receive radiation or observation (rapid early responders only), or they received two further rounds of ABVE-PC, two rounds of dexamethasone, etoposide, cisplatin, and cytarabine (DECA), and IFRT (slow early responders only). Lung toxicities were reported following each cycle, according to the toxicity scale of the National Cancer Institute Common Terminology Criteria for Adverse Events v2.

DMET Genotyping:
Genotyping was performed using gDNA extracted from blood using the Puregene Qiagen Blood DNA extraction kit.

Figure 2:
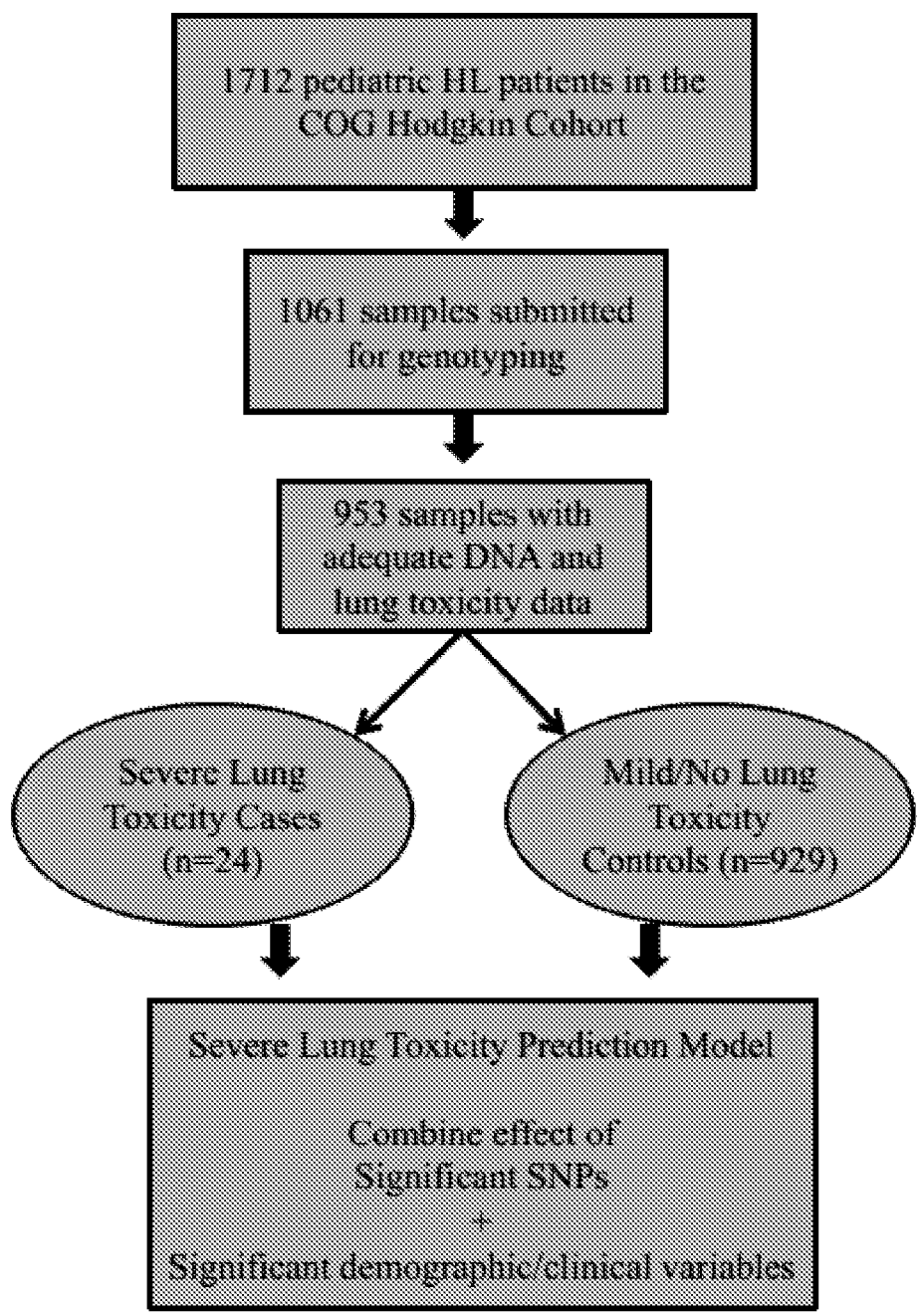
FIG. 2. Flow chart of case-control patient selection.

All samples were genotyped using The Drug Metabolizing Enzymes and Transporters (DMET™) Plus Premier Pack (Affymetrix, Santa Clara, Calif., USA) designed to probe 1,936 SNPs in 225 high-value drug metabolism and transporter genes. The preparation and processing protocol for patient samples was performed under CLIA-compliant conditions in a clinical genetics laboratory at the Cincinnati Children's Hospital according to manufacturer guidelines. The array scan data was analyzed with the Affymetrix DMET™ Console software, using the dynamic calling algorithm to assign genotype information based on cluster boundaries. A total of 1061 patient samples were submitted for genotyping; 953 had adequate DNA (FIG. 2). Other methods by which SNPs may be detected are described in, for example, US Patent Publication 2012/0014956.

Statistical Methods:
The maximum reported toxicity at any treatment cycle among four lung-related toxicities, including carbon monoxide diffusion capacity (DLCO), dyspnea, forced expiration volume (FEV1), and hypoxia, was taken as an individual's lung toxicity severity. Severity ranged from zero (no toxicity) to four (life-threatening), and was dichotomized with a cutoff designed to distinguish no/mild events (grade 0-2, n=929) from severe events (grade 3-4, n=24). Dichotomized lung toxicity served as the primary outcome variable.

For descriptive purposes, Applicant tested the pairwise association between dichotomized lung toxicity severity and multiple demographic and clinical variables, phase one response (slow-early responder vs rapid-early responder) and exposure to IFRT. T-tests and chi-square tests were used where appropriate. To determine potentially meaningful covariates for inclusion in genetic association analysis Applicant employed stepwise regression analysis; all demographic/clinical variables were considered as possible covariates (entry p-value cutoff=0.2, significance p-value cutoff=0.1). Significant or trending variables were included as covariates during all phases of genetic association analysis.

All DMET SNPs (n=1931) were filtered based on quality parameters, including minor allele frequency >0.05 (1277 excluded SNPs), Hardy-Weinberg p-value >0.001 (79 SNPs excluded), and missing rate <0.1 (13 SNPs excluded), leaving 563 SNPs with an overall genotyping frequency of 0.994 to test across 24 cases and 929 controls (several SNPs failed multiple quality filtrations). Pairwise association between each SNP and dichotomized lung toxicity severity was tested using PLINK's logistic association analysis, which compares allele frequency between cases and controls, rather than assuming an effect model (e.g. dominant, recessive). In order to remove the effect of possible population substructure on association results, estimates were produced through empirical permutation methods. Linkage disequilibrium and functionality of SNPs with nominal empirical significance (p<0.005) was tested. In the case of SNP redundancy ($R^2$>0.8), the SNP with clear functional implications or highest significance was carried forward for further analysis.

Figure 6:
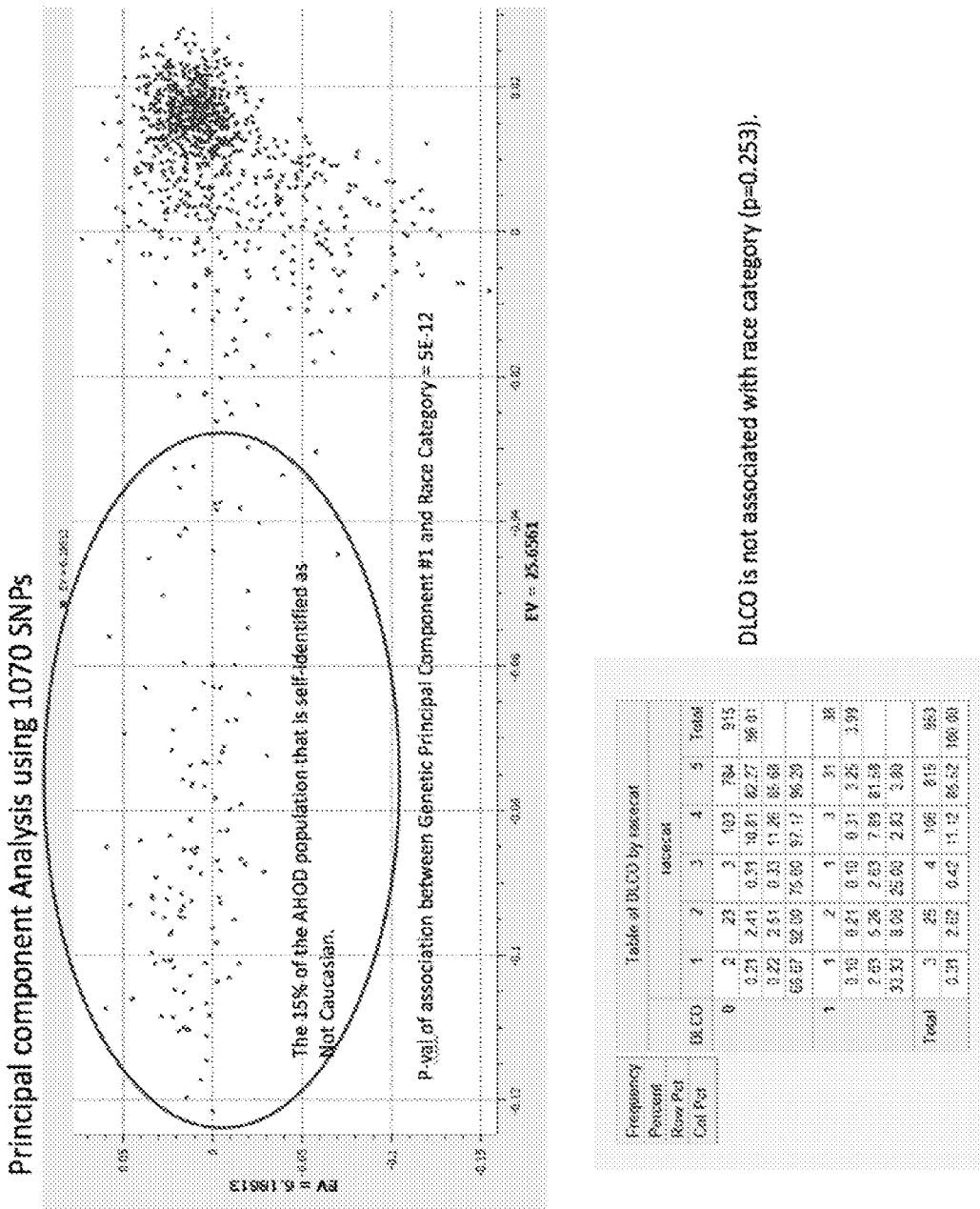
FIG. 6. Scatterplot of principal components 1 and 2 generated through principal component analysis applied to high-quality SNPs for the prediction of racial subgroups, demonstrating the population substructure within the COG Hodgkin cohort.
Figure 7:
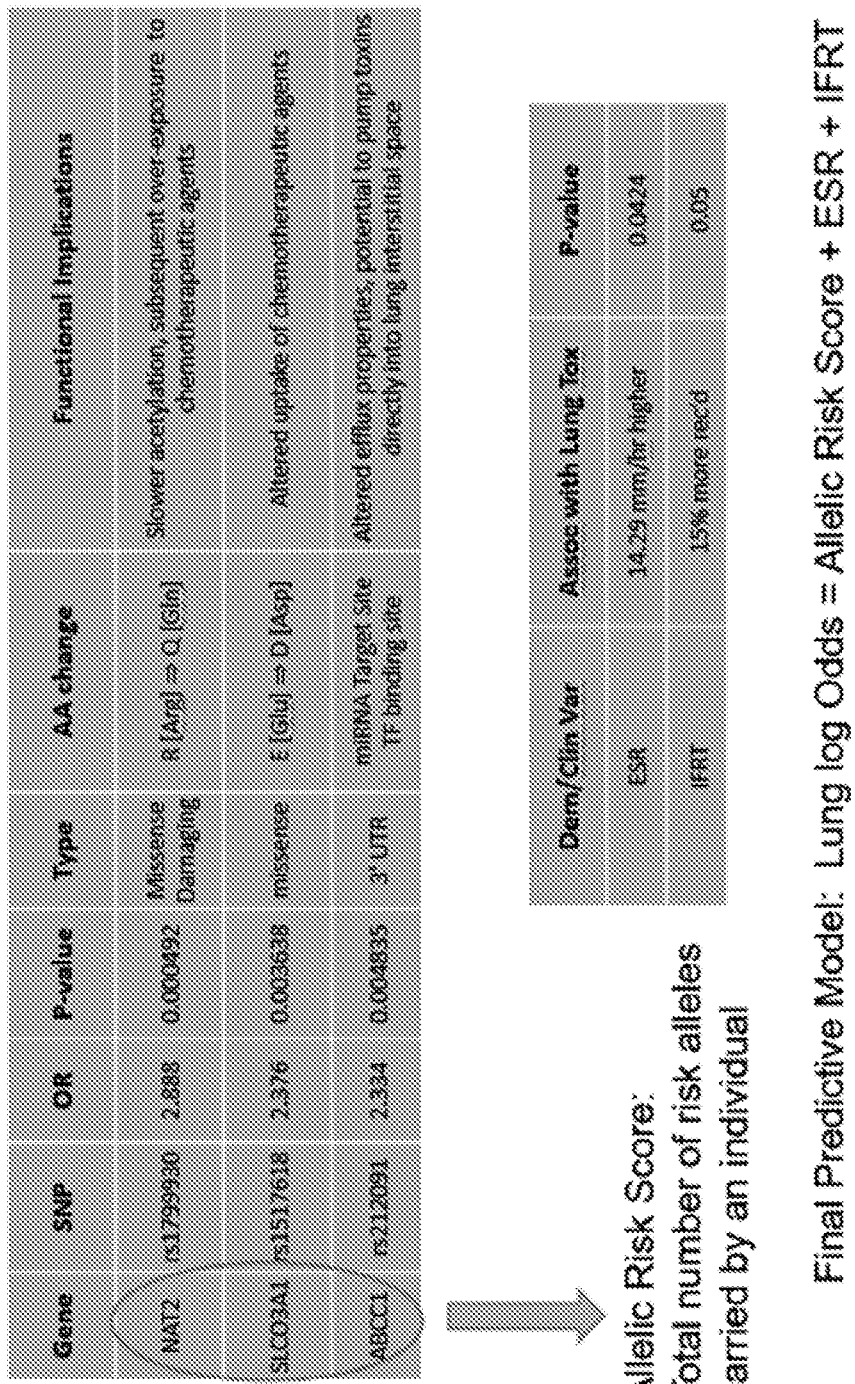
FIG. 7. Schematic showing final predictive model.
Figure 8:
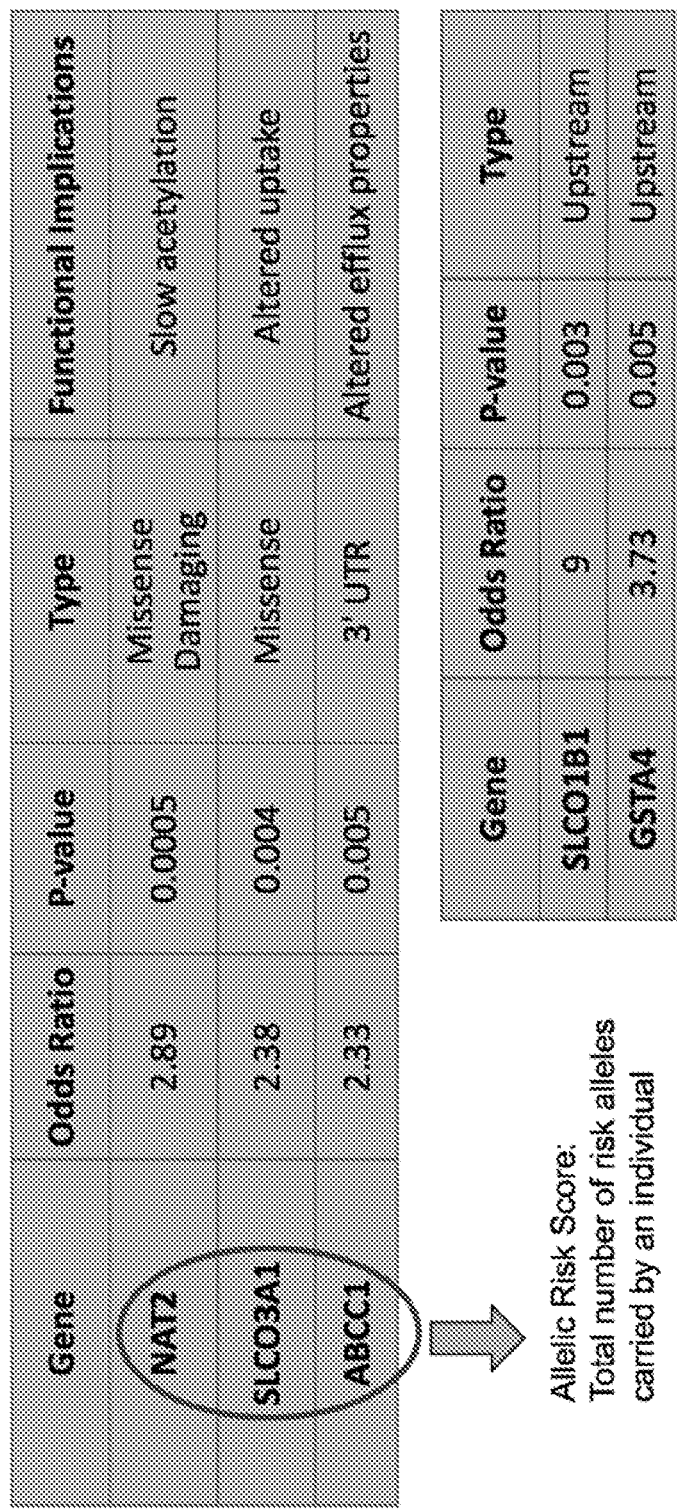
FIG. 8. Schematic showing final predictive model for high risk including SLCO1B1 and GSTA4.
Figure 9:
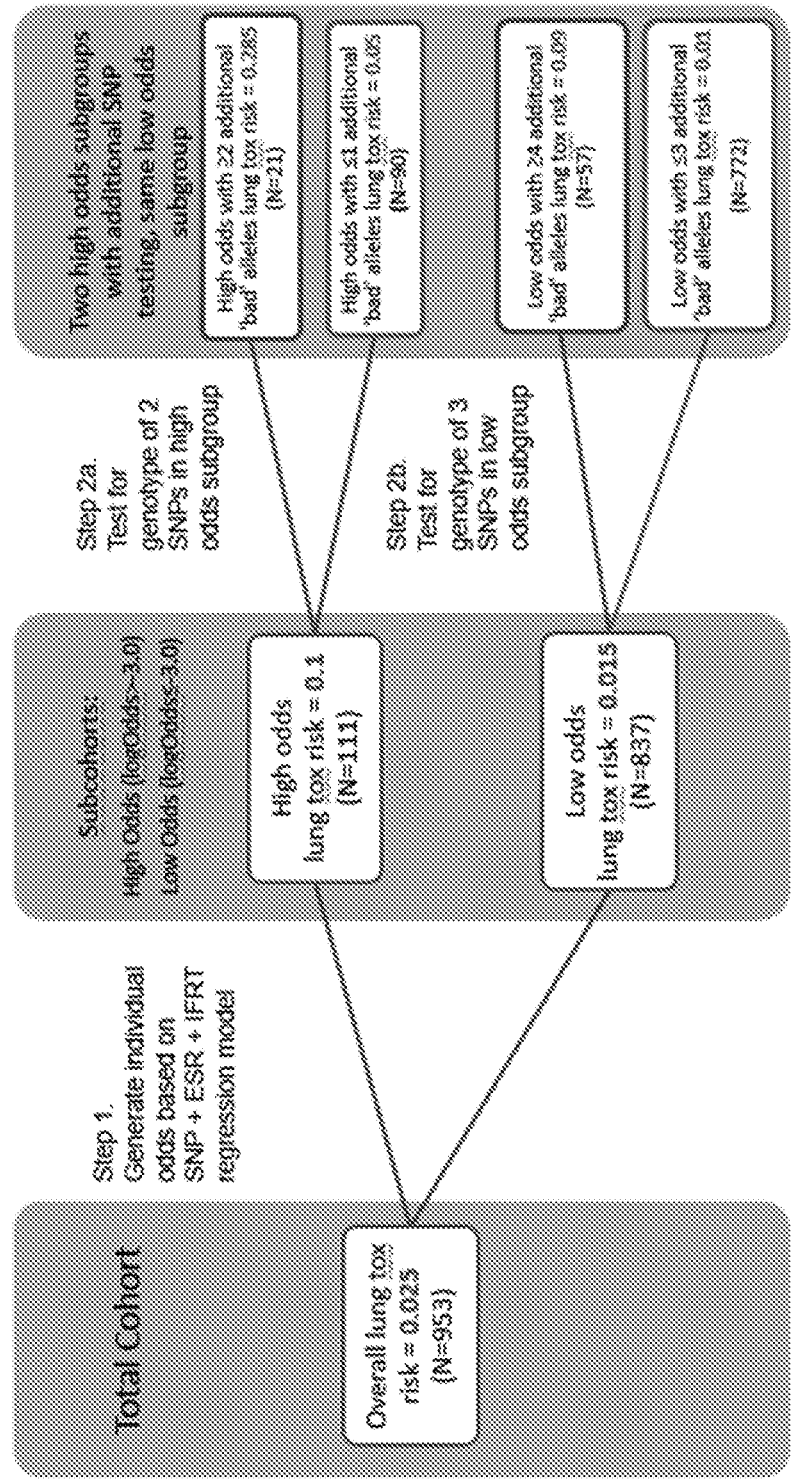
FIG. 9. Schematic showing two step testing protocol.
Figure 10:
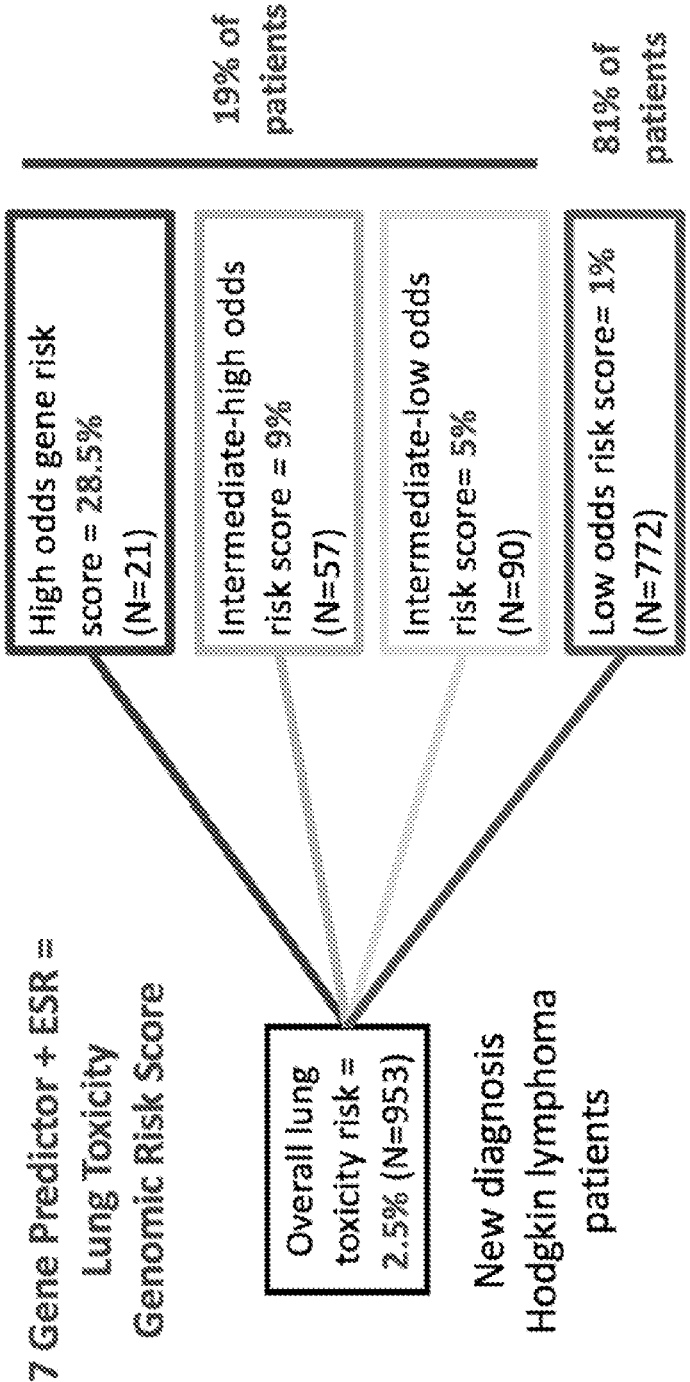
FIG. 10. Schematic showing use of lung gene risk score to select Hodgkin therapy.
Figure 11:
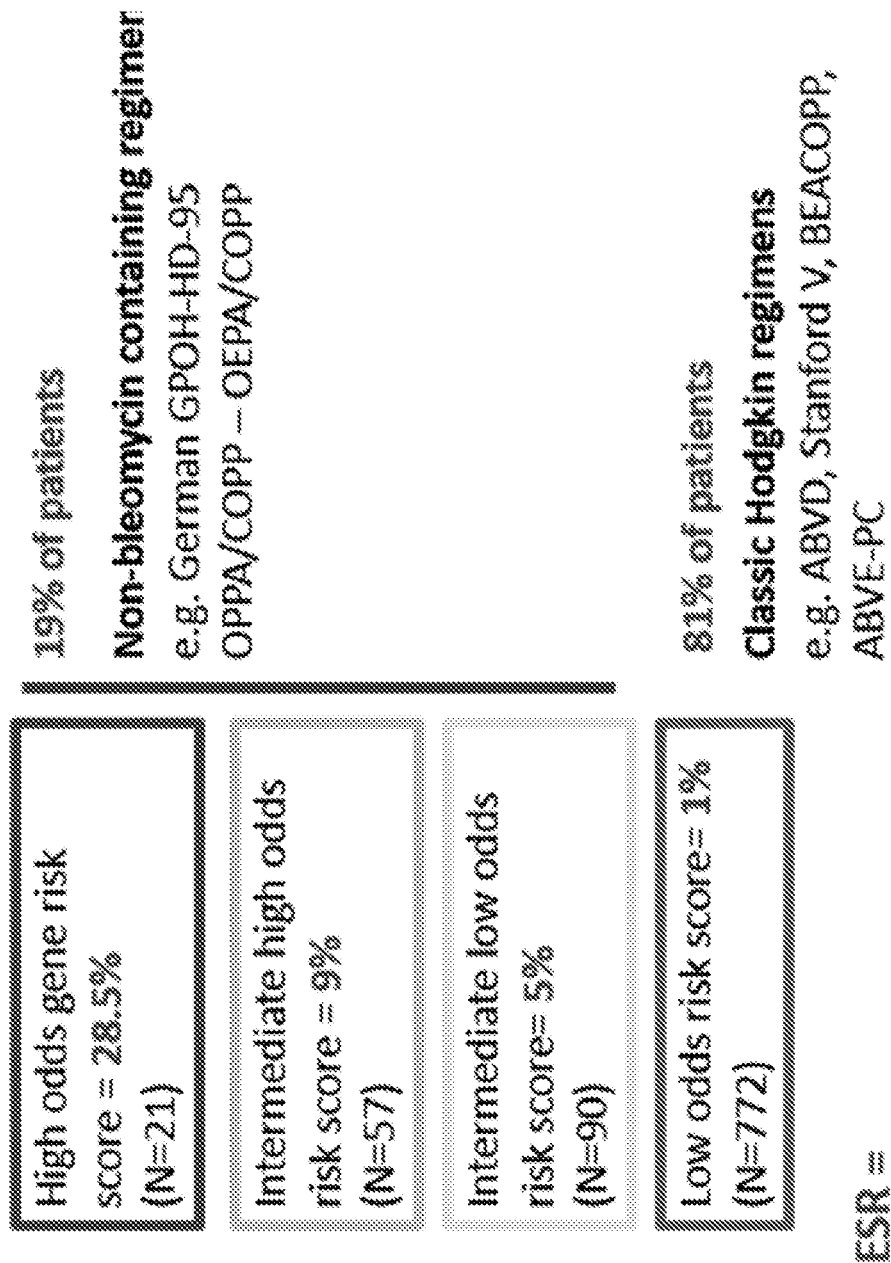
FIG. 11. Schematic showing using the Lung Gene Risk Score to select Hodgkin Therapy.

Applicant determined through principal component analysis that the cohort was comprised of two general subpopulations that correspond to self-reported race; African American individuals showed a distinct genetic profile compared to all other races in the cohort (FIG. 6). Appropriate steps were taken to correct for population stratification (estimate permutation and conditional regression analysis).

A per-individual allelic risk score was generated based on the number of risk alleles carried by each individual. The number of risk alleles per SNP ranged from zero to two, and these were summed across all significant, non-redundant SNPs. Conditional logistic regression analysis was used to generate prediction models, which included previously identified demographic/clinical covariates and the allelic risk score while correcting for population substructure. Non-significant variables were dropped with a p-value cutoff of 0.05. Due to the low number of toxicity events, Applicant performed bootstrapping analysis that generated 1000 new data sets from Applicant's original data (one to one sampling with replacement), to provide further confidence to Applicant's results. Conditional logistic regression was performed in each data set to determine the validity of Applicant's original model variables and their point estimates. Applicant's single-model point estimates and their 95% confidence intervals were compared to the mean and 95% confidence intervals computed from all bootstrapped model estimates. Model fit at each step was assessed through the model fit statistic Akaike Information Criterion (AIC), which incorporates goodness-of-fit and model complexity.

Univariate genetic association analysis was performed in PLINK v1.9. All other analyses were performed in SAS v9.3.

Results

A nested case-control study consisted of 953 individuals aged 2 to 21 years with lung toxicity information and DMET genotyping available. Of these, 186 individuals had a lung toxicity of any grade; 24 individuals had a lung toxicity score of three or greater (Table 1).

There were 180 DLCO events (15 severe) and 11 dyspnea events (six severe), two FEV1 events (one severe), and four hypoxia events (all severe). Two individuals had multiple severe lung toxicities reported. A single life-threatening event was reported (dyspnea, level 4) but no lung toxicity-related deaths. All but one severe event was reported during an ABVE-PC cycle; one was reported during a DECA cycle (Table 2).

Through univariate association testing, erythrocyte sedimentation rate (ESR) was found to be was significantly associated with lung toxicity (p=0.0454), where elevated sedimentation conferred increased risk, although exposure to IFRT was marginally associated with increase in risk toxicity (p=0.053, Table 2). Temporally, IFRT was administered after all observed severe lung toxicities, indicating the near-association was random. Following a stepwise regression model building beginning with all baseline demographic and clinical information, Applicant found that ESR alone was a significant covariate.

Of the 563 SNPs that passed quality filtration, four SNPs with a p-value <0.005 after controlling for the effects of ESR and population substructure were found (Table 3). Of these four, two SNPs in NAT2 were in high LD ($R^2$=0.9); the SNP with higher significance and stronger functional implications (rs1799930, p=0.0005, nonsynonymous) was selected for further analysis. The remaining two SNPs included a nonsynonymous SNP in SLCO3A1 (rs1517618, p=0.0036) and a SNP in the 3' untranslated region of ABCC1 (rs212091, p=0.0048). An Allelic Risk Score was computed for each individual (the risk allele for each significant SNP was also the minor allele), which ranged from zero to five.

Figure 3:
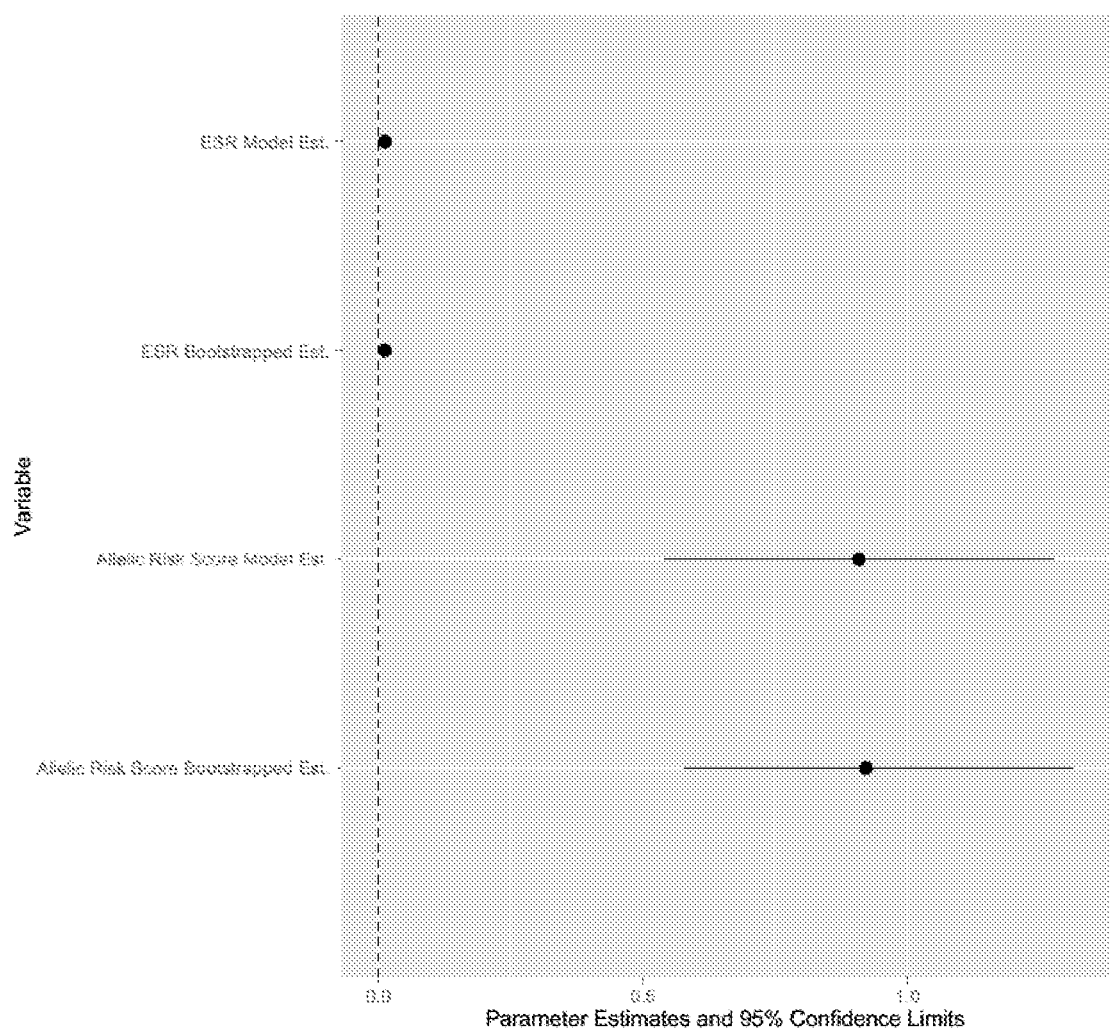
FIG. 3. Forest plot of conditional logistic regression point estimates and 95% confidence intervals with means and 95% confidence intervals computed from estimates generated from testing the model over 1000 bootstrapped data sets.

A predictive regression model (conditional on self-reported race) was built that included the Allelic Risk Score and ESR (Table 5). Elevated baseline ESR was found to confer increased risk for lung toxicity (each additional 10 mm/hr sedimentation increased toxicity odds by 1.15, p=0.01) and each additional risk allele increased the odds for lung toxicity by 2.19 (p<0.0001). The overall model chi-square was 21.43 with p<0.0001 (AIC=198.75). Bootstrapped parameter estimates showed strong agreement with Applicant's point estimates (FIG. 3). The final model exhibited an area under the curve of 0.76.

Figure 4:
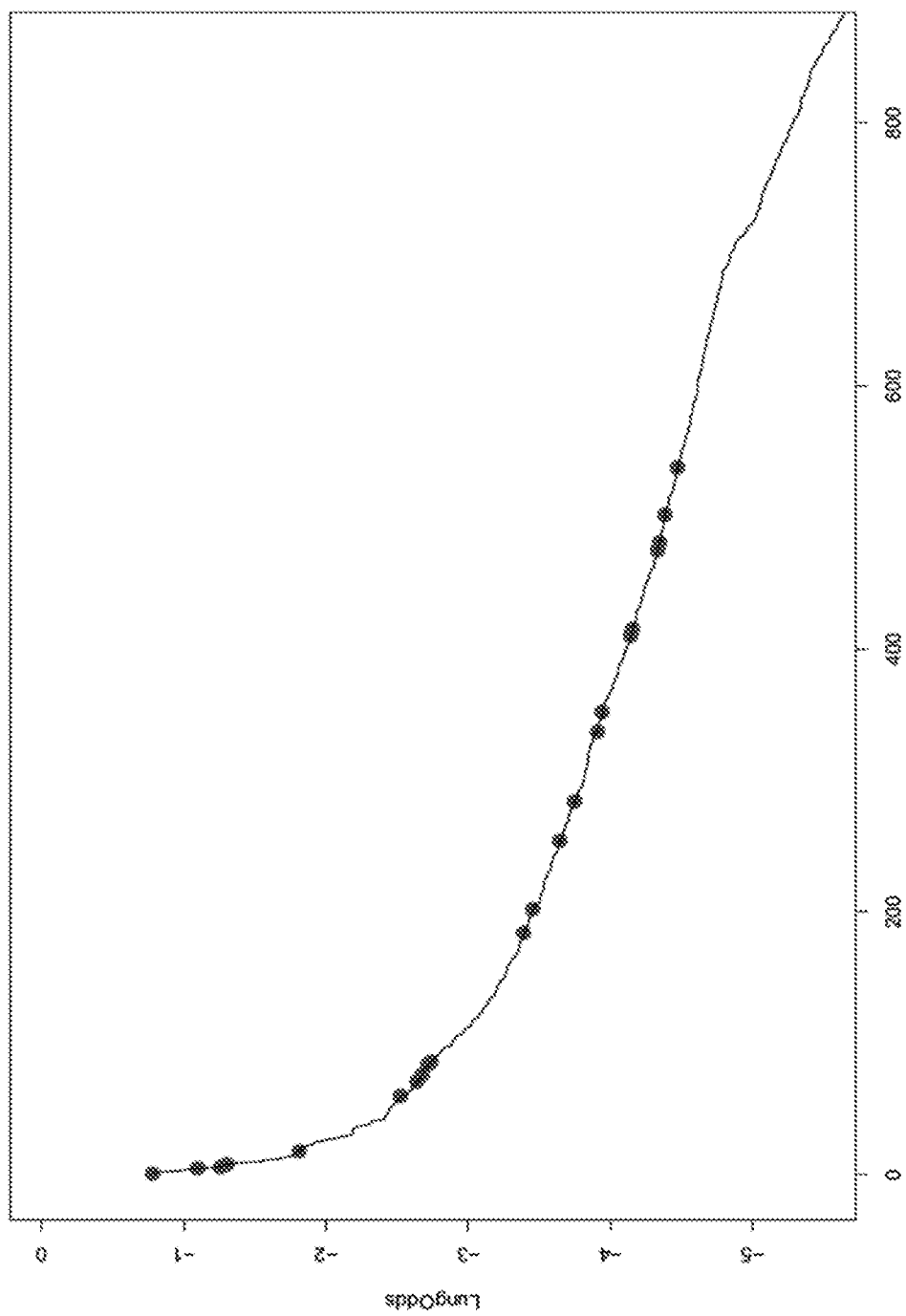
FIG. 4. Plot of per-individual log-odds derived from the predictive model based on allelic risk score and erythrocyte sedimentation rate. Red indicates the individual experienced a severe lung toxicity.

Lung toxicity log odds were computed for each individual based on the final conditional logistic regression model. Through observation of the log-odds distribution in the population (FIG. 4), Applicant identified two distinct risk groups that could be identified as having log-odds scores ≥-3 (high risk) or ≤-3 (low risk). Of high-risk individuals 24.1% had lung toxicities of any grade, while 9.8% had severe lung toxicities. Among low-risk individuals 18.9% had lung toxicities of any grade, while only 1.54% had severe lung toxicities.

Re-testing of univariate associations between SNPs and lung toxicity constrained to the high-risk subgroup revealed two strongly-associated SNPs (p<0.01), whose minor alleles conferred increased risk for severe lung toxicity (rs13197674 and rs4149015 in GSTA4 and SLCO1B1, respectively; Table 7).

No severe lung toxicities were observed in individuals who lacked any minor (risk) alleles in these SNPs. The presence of a single risk allele from either of these SNPs increased the odds for toxicity to 0.10; individuals with two or three risk alleles had odds of 0.286 (Table 8). The odds ratio between individuals with one or fewer risk alleles and those with two or more risk alleles was 4.85. Within the low-risk group, Applicant identified four SNPs significantly associated with severe lung toxicity (p<0.01); rs5305 and rs4736312 in CYP11B1, rs2268873 in SLC7A8, and rs2291075 in SLCO1B1 (Table 7).

From summed risk alleles across three non-redundant SNPs (the SNPs in CYP11B1 were in near-perfect LD), Applicant determined that the odds for toxicity in individuals with >4 risk alleles was 0.087, compared to odds of 0.01 in those with <4 risk alleles (odds ratio of 8.55; Table 8). Due to the very low prevalence of severe lung toxicity in the low-risk subgroup, generation of a high-precision allelic risk score was unlikely.

A two-step process may be implemented at baseline for the identification of patients genetically predisposed to severe lung toxicity, starting with the primary regression model followed by an assessment for two or more risk alleles in the GSTA4 and SLCO1B1 SNPs in the high risk group and four or more risk alleles in the CYP11B1, SLC7A8, and SLCO1B1 SNPs. Within the AHOD0031 cohort, this process results in the identification of individuals with severe lung toxicity with a sensitivity of 0.458 and specificity of 0.927 (positive predictive value of 0.141 and negative predictive value of 0.985).

DISCUSSION

Disclosed are methods for the improved identification of pediatric Hodgkin's lymphoma patients at increased risk for severe lung toxicities due to therapeutic agents. Using baseline demographic information, clinical characteristics, and DMET SNPs, a predictive clinical model that includes three drug metabolism SNPs in NAT2, SLCO3A1, and ABCC1 was developed. All variants carry clear functional implications; the SNPs in NAT2 and SLCO3A1 were non-synonymous (Arg to Gln and Glu to Asp, respectively) and the variant in ABCC1 alters binding motifs for EBF, GR, ATF3, and RFX5 in addition to altering miRNA target sites.

Genetic variation within Applicant's most significant gene, NAT2, results in slow and fast acetylation phenotypes, and directly affects the degree of exposure to a therapeutic agent.[10] NAT2 variants have been connected to antituberculosis drug hepatotoxicity,[11] and implicated as an effect-modifier of oxidant exposures leading to male infertility and of several toxicants associated with diverse cancers.[12, 13] The rs1799930 variant results in a profound alteration in the amino acid sequence, from large and basic arginine to medium-sized and polar glutamine. The arginine (minor/risk variant in Applicant's cohort) is associated with a slow acetylation phenotype, which may result in over-exposure to chemotherapeutic agents and subsequent toxicities.

SLCO3A1 is a ubiquitously expressed sodium-independent organic anion transporter, mediating uptake of diverse endogenous and exogenous compounds, including chemotherapeutic agents. OAT3A1, the protein encoded by SLCO3A1, is upregulated in cancerous tissues (likely to facilitate hormone transport), and has implications in drug resistance and dependence.[14] The rs1517618 variant results in a protein with similar physic-chemical properties, both acidic and medium-sized residues. The effect of the variant may be directly due to the protein alteration, or attributable to three binding motifs (AP-1, LF-A1, and p300) altered by the nucleotide change.

Finally, ABCC1 is a well-described member of the ABC-cassette transporter family, which are extra- and intra-cellular membrane transporters. The association between ABCC1 variants and the protein's efflux properties are clearly documented;[15, 16] additionally, variants in the 3' untranslated region have been associated with lung cancer through interaction effects with tobacco-specific exposures.[17] The rs212091 variant lies within a cluster of miRNA targets (TargetScan and UCSC genome browser; miR-133abc, miR-7ab, miR-199ab-5p, miR-145, miR-217).[18-22] All of these microRNAs have documented expression in the lung and have been implicated in pulmonary abnormalities,[19, 23-25] providing potential insight into the 3'UTR variant's effect on ABCC1 expression and function. Additionally, ABCC1 is expressed in the basolateral membrane of the epithelium and can pump toxins directly into the lung interstitial space.

Of the variants conferring increased toxicity risk in the high-risk/high log-odds population subset, both SNPs are located 2kb upstream of their respective genes. Variants in both genes have been previously associated with drug-induced toxicity and fibrosis in the liver.[26, 27] Within the low-risk/low log-odds population subset, a risk SNP near CYP11B1 was identified; variation in this gene has been implicated in lung development.[28] This may imply a developmental deficit in the lung predisposes toward injury during chemotherapy. Applicant also observe a significant variant within the first intron of SLC7A8, located within an H3k27Ac binding site, that may impact binding of multiple transcription factors (MYC and ZNF217). Previously, this gene has been connected to pulmonary inflammation through mast cell activation.[29] Finally, a synonymous variant within the $6^{th}$ exon of SLCO1B1 (which encodes OATP2) was identified; variants in this gene were significant in high- and low-risk individuals, indicating a central mechanism of delayed drug clearance through altered OATP2 function.

Figure 5:
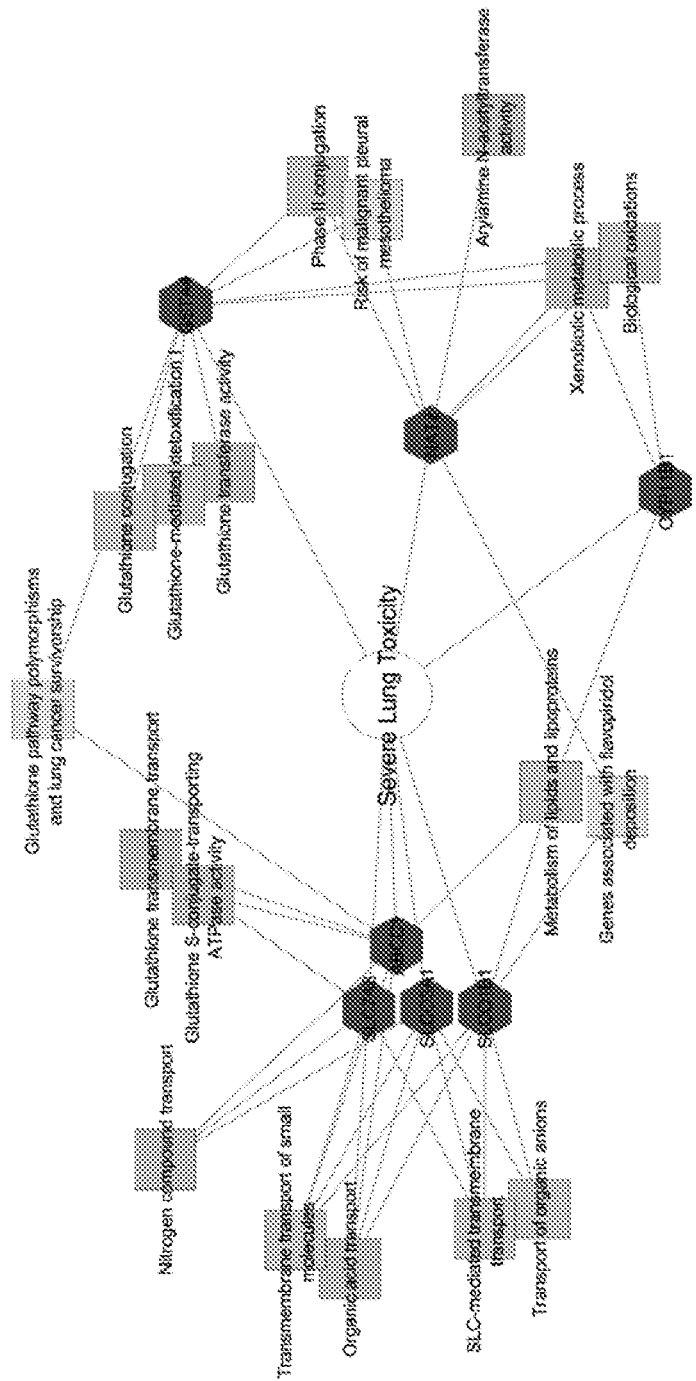
FIG. 5. Network diagram showing genes with severe lung toxicity-associated SNPs and their functional annotations.

Through an ontological analysis focusing on genes with variants strongly associated with severe lung toxicity (toppgene.cchmc.org), Applicant provides some insight into the biological underpinnings of chemotherapeutic-induced severe lung toxicity (FIG. 5). The gene network indicates an integrated impact of disruption in mechanisms related to lung development, drug metabolism, and drug transport. In particular, Applicant's analysis may point to glutathione as a key molecule in the development of chemotherapy-induced lung toxicity.

In addition to the genetic factors that predispose toward lung toxicity, Applicant found elevated ESR further increased risk. With a non-specific test for inflammation clinicians are somewhat limited in defining direct implications of elevated sedimentation. However, the disclosed results agree with a previous report of elevated ESR preceding chemotherapy-induced pulmonary toxicity,[30] suggesting ESR may be a useful marker for chemotherapeutic and steroid selection-guidance.

Conclusion

Using baseline clinical and genetic information in a large pediatric Hodgkin cohort, Applicant has developed a model for the identification of individuals at elevated risk for severe lung toxicities during treatment for Hodgkin Lymphoma. Using ESR and a combinatory score built from SNPs in NAT2, SLCO3A1, and ABCC1, and subsequent testing for variants in GSTA4, SLCO1B1, CYP11B1, and SLC7A8 individuals with genetic predisposition for toxicity can be identified and treated appropriately. Since alternate drug therapies are available that carry lower risk for lung toxicities, these results may provide a starting point for a genetically-guided therapeutic regimen for the treatment of Hodgkin Lymphoma while minimizing pulmonary side-effects.

TABLE 1

Distribution of toxicity grades across specific lung toxicities.

| Toxicity Level | DLCO | Dyspnea | FEV1 | Hypoxia |
|---|---|---|---|---|
| 0 | 773 | 942 | 951 | 949 |
| 1 | 82 | 0 | 0 | 0 |
| 2 | 52 | 5 | 1 | 0 |
| 3 | 15 | 5 | 1 | 4 |
| 4 | 0 | 1 | 0 | 0 |
| 5 | 0 | 0 | 0 | 0 |
| Total Events | 149 | 11 | 2 | 4 |
| Total Severe Events | 15 | 6 | 1 | 4 |

TABLE 2

Distribution of severe and mild lung toxicities across ABVE-PC, DECA, and IFRT.

| Toxicity Severity | ABVE-PC Cycles 1, 2 | ABVE-PC Cycles 3, 4 | DECA | IFRT |
|---|---|---|---|---|
| Severe DLCO | 4 | 11 | 1 | 0 |
| Severe Dyspnea | 1 | 1 | 0 | 0 |
| Severe FEV1 | 1 | 0 | 0 | 0 |
| Severe Hypoxia | 3 | 1 | 0 | 0 |
| No/Mild DLCO | 949 | 906 | 88 | 655 |
| No/Mild Dyspnea | 952 | 916 | 89 | 655 |
| No/Mild FEV1 | 952 | 917 | 89 | 655 |
| No/Mild Hypoxia | 950 | 916 | 89 | 655 |

TABLE 3

Demographic and clinical characteristics of the case-control subset of the AHOD cohort. Continuous variables are reported as mean (standard deviation); median (interquartile range). Binary traits are reported as number (percent). Each trait was tested for univariate association with severe lung toxicity; significant p-values are denoted with *.

| Clin/Demographic Information | Total Population | No/Mild Lung Toxicity (N = 929) | Lung Toxicity Grade 3-4 (N = 24) | P-value |
|---|---|---|---|---|
| Sex (n = 953) | | | | |
| Male | 509 (53·41%) | 497 (52·15%) | 12 (1·26%) | 0·734 |
| Female | 444 (46·59%) | 432 (45·33%) | 12 (1·26%) | |
| Race (n = 953) | | | | |
| African American | 106 (11·12%) | 103 (10·81%) | 3 (0·31) | 0·828 |
| Not African American | 847 (88·88%) | 826 (86·67%) | 21 (2·2%) | |
| Mediastinal Mass (n = 918) | | | | |
| Yes | 381 (41·5%) | 368 (40·09%) | 12 (1·42%) | 0·202 |
| No | 537 (58·5%) | 526 (57·3%) | 11 (1·2%) | |
| Received IFRT (n = 953) | | | | |
| Yes | 655 (68·73%) | 635 (66·63%) | 20 (2·1%) | 0·057 |
| No | 298 (31·27%) | 294 (30·85%) | 4 (0·42%) | |
| Bulk Disease (n = 941) | | | | |
| Yes | 723 (76·83%) | 704 (74·81%) | 19 (2·02%) | 0·783 |
| No | 218 (23·17%) | 231 (22·64%) | 5 (0·53%) | |
| B Symptoms (n = 953) | | | | |
| Yes | 200 (20·99%) | 195 (20·46%) | 5 (0·52%) | 0·985 |
| No | 753 (79·01%) | 734 (77·02%) | 19 (1·99%) | |
| Extralymphatic Disease (n = 898) | | | | |
| Yes | 191 (21·27%) | 188 (20·94%) | 3 (0·33%) | 0·488 |
| No | 707 (78·73%) | 690 (76·84%) | 17 (1·98%) | |
| Fever (n = 947) | | | | |
| Yes | 86 (9·08%) | 83 (8·76%) | 3 (0·32%) | 0·555 |
| No | 861 (90·92%) | 840 (88·70%) | 21 (2·22%) | |
| Night Sweats (n = 952) | | | | |
| Yes | 131 (13·76%) | 130 (13·66%) | 1 (0·11%) | 0·234 |
| No | 821 (86·24%) | 798 (83·82%) | 23 (2·42%) | |

TABLE 3-continued

Demographic and clinical characteristics of the case-control subset of the AHOD cohort. Continuous variables are reported as mean (standard deviation); median (interquartile range). Binary traits are reported as number (percent). Each trait was tested for univariate association with severe lung toxicity; significant p-values are denoted with *.

| Clin/Demographic Information | Total Population | No/Mild Lung Toxicity (N = 929) | Lung Toxicity Grade 3-4 (N = 24) | P-value |
|---|---|---|---|---|
| Weight Loss (n = 946) | | | | |
| Yes | 77 (8•14%) | 74 (7•82%) | 3 (0•32%) | 0•436 |
| No | 869 (91•86%) | 848 (89•64) | 21 (2•22%) | |
| Nodal Aggregation (n = 922) | | | | |
| Yes | 533 (57•81%) | 520 (56•40%) | 13 (1•41%) | 0•714 |
| No | 389 (42•19%) | 378 (41%) | 11 (1•19%) | |
| Age at Diagnosis (yrs; n = 953) | 14•087 (3•28); 15•00 (12-16) | 14•08 (2•39); 15•00 (12-16) | 14•21 (3•27); 15•00 (12-17) | 0•855 |
| Hemoglobin (n = 928) | 11•841 (1•74 ); 11•90 (10•7-13•0) | 11•85 (1•74); 1•90 (10•7-13•00) | 11•60 (1•62); 11•75 (10•85-12•45) | 0•497 |
| Erythrocyte Sedimentation Rate (n = 899) | 48•63 (33•36 ); 42•00 (22-67) | 48•22 (33•10); 42•00 (22-67) | 62•57 (40•27); 45•00 (32-98) | 0•0424* |
| Albumin (n = 909) | 3•752 (0•62); 3•80 (3•4-4•2) | 3•76 (0•615); 3•800 (3•4-4•2) | 3•59 (0•64); 3•80 (3•05-4•05) | 0•196 |

TABLE 4

Allelic information for all SNPs significantly associated with severe lung toxicity, including major and minor allele, minor allele frequency (MAF), odds ratio (OR) associated with the minor allele, and functional implications of the variant.

| SNP | Minor Allele | Major Allele | MAF | OR | Statistic | p-value | Type | Gene | Functional Implication |
|---|---|---|---|---|---|---|---|---|---|
| rs1799930 | A | G | 0.263 | 2.888 | 3.484 | 0.000492 | missense | NAT2 | R [Arg] ⇒ Q [Gln] |
| rs1517618 | G | C | 0.145 | 2.376 | 2.613 | 0.003638 | missense | SLCO3A1 | E [Glu] ⇒ D [Asp] |
| rs1041983 | T | C | 0.333 | 2.397 | 2.873 | 0.003863 | synonymous | NAT2 | Y [Tyr] ⇒ Y [Tyr] |
| rs212091 | G | A | 0.153 | 2.334 | 2.532 | 0.004835 | 3' UTR | ABCC1 | EBF, GR, ATF3, RFX5 binding |

TABLE 5

Distribution of allelic risk scores across individuals with no/mild lung toxicities or severe lung toxicities.

| Allelic Risk Score | Mild/No Lung Tox | Severe Lung Tox | Total |
|---|---|---|---|
| 0 | 273 | 1 | 0•004 |
| 1 | 385 | 7 | 0•018 |
| 2 | 196 | 7 | 0•034 |
| 3 | 60 | 6 | 0•091 |
| 4 | 14 | 2 | 0•125 |
| 5 | 1 | 1 | 0•5 |
| Total | 929 | 24 | |

TABLE 6

Estimates, odds ratios, and significance statistics for predictors of severe lung toxicities included in the final conditional logistic regression model.

| Predictor | Estimate | Odds Ratio | Chi-Square | p-value |
|---|---|---|---|---|
| Intercept | −5.735 | NA | 90.354 | <0.0001 |
| Risk Score | 0•907 | 2•193 | 23•408 | <0•0001 |
| ESR | 0•0153 | 1•015 | 4•115 | 0•01 |

TABLE 7

Allelic information for all SNPs significantly associated with
severe lung toxicity in high- and low-risk subgroups, including major
and minor allele, minor allele frequency (MAF), odds ratio (OR)
associated with the minor allele, and functional implications of the variant.

| Risk Group | SNP | Minor Allele | Major Allele | MAF | OR | Statistic | P-value | Type | Gene | Functional Implications |
|---|---|---|---|---|---|---|---|---|---|---|
| High Risk | rs4149015 | A | G | 0.054 | 9 | 2.87 | 0.002938 | Upstream | SLCO1B1 | Unknown |
| High Risk | rs13197674 | G | A | 0.369 | 3.725 | 2.566 | 0.005548 | Upstream | GSTA4 | Numerous TFs binding |
| Low Risk | rs5303 | T | C | 0.389 | 2.921 | 2.606 | 0.00193 | 3' UTR | CYP11B1 | Posttranslational modification |
| Low Risk | rs2268873 | C | T | 0.221 | 2.599 | 2.383 | 0.005994 | Intronic | SLC7A8 | MYC, ZNF217 binding |
| Low Risk | rs2291075 | T | C | 0.407 | 0.2637 | −2.446 | 0.008725 | Synonymous | SLCO1B1 | Unknown |
| Low Risk | rs4736312 | T | C | 0.415 | 2.635 | 2.355 | 0.009349 | 3' UTR | CYP11B1 | Posttranslational modification |

TABLE 8

Distribution of allelic risk scores between individuals
with and without severe lung toxicity, using SNPs uncovered
in secondary testing in high- and low-risk subsets.

| Allelic Risk Score | No Toxicity | Toxicity | Odds |
|---|---|---|---|
| High-Risk Subgroup | | | |
| 0 | 41 | 0 | 0 |
| 1 | 44 | 5 | 0.102041 |
| 2 | 13 | 5 | 0.277778 |
| 3 | 2 | 1 | 0.333333 |
| Low-Risk Subgroup | | | |
| 0 | 56 | 0 | 0 |
| 1 | 210 | 0 | 0 |
| 2 | 292 | 2 | 0.007 |
| 3 | 214 | 6 | 0.027 |
| 4 | 52 | 4 | 0.071 |
| 5 | 0 | 1 | 1 |

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

The risk level in an individual for lung toxicity associated with bleomycin treatment is determined, wherein the individual has a proliferative disorder, wherein the risk level is determined based on the presence or absence of one or more polymorphisms in one or more genes selected from NAT2, SLCO1B1, ABCC1, GSTA4, CYP11B1, SLC7A8, and SLCO3A1, and the erythrocyte sedimentation rate (ESR) in a biological sample of the individual. The risk level is calculated based on the presence or absence of said polymorphism in combination with the ESR, wherein when said individual is characterized as high risk for bleomycin-associated lung toxicity, said individual is treated with a protocol that does not contain bleomycin, and wherein when said individual is characterized as low risk for bleomycin-associated lung toxicity, said individual is treated with a protocol that contains bleomycin.

Example 2

The method of Example 1 wherein the polymorphism is a single nucleotide polymorphism selected from rs1799930 in NAT2, rs1041983 in NAT2, rs2291075 in SLCO1B1, rs212091 in ABCC1, rs13197674 in GSTA4, rs4149015 in GSTA4, rs4736312 in CYP11B2, rs5305 in CYP11B1, rs2268873 in SLC7A8, rs1517618 in SLCO3A1, or a combination thereof.

Example 3

The method of Example 1 or 2, wherein the identification step comprises identifying a first allelic risk score based on identification of a polymorphism in NAT2, SLCO3A1, and ABCC1.

Example 4

The method of Example 1, 2 or 3, wherein the presence of a polymorphism in NAT2, SLCO3A1, and/or ABCC1 is used to generate an allelic risk score ranging from 0 to 5.

Example 5

The method of any of Examples 1-4, wherein said erythrocyte sedimentation rate (ESR) is used to calculate a log-odds score, wherein a sedimentation rate increase of 10 mm/Hg increases a log-odds score by 1.15, and wherein said log-odds score is used to identify high risk and low risk individuals.

Example 6

The method of any preceding Example, wherein the protocol that does not include the use of bleomycin is vincristine (Oncovin), etoposide, prednisone, doxorubicin (Adriamycin) ("OEPA").

Example 7

The method of any preceding Example, wherein said protocol that does not include the use of bleomycin is cyclophosphamide, vincristine, prednisone, dacarbazine (Dac), ("COPDac").

Example 8

The method of any preceding Example, wherein an individual is characterized as having a high risk for lung toxicity if a log-odds score of ≥−3 for said individual is determined.

Example 9

The method of any preceding Example, wherein an individual is characterized as having a low risk for lung toxicity if a log-odds score of <−3 for said individual is determined, wherein the high-risk individual is treated with bleomycin.

Example 10

The method of any preceding Example, wherein the biological sample is any biological fluid containing DNA.

Example 11

The method of any preceding Example, wherein the biological sample is selected from a tissue, a cell, blood, saliva, or a combination thereof.

Example 12

The method of any preceding Example, wherein said identification step is carried out using a primer complementary to a polymorphism selected from any one of Example 3.

Example 13

The method of any preceding Example, wherein said identification step is carried out using at least two primers complementary to at least two polymorphisms of Example 3, or at least three primers complementary to at least three polymorphisms of Example 3, or at least four primers complementary to at least four polymorphisms of Example 3, or at least five primers complementary to at least five polymorphisms of Example 3, or at least six primers complementary to at least six polymorphisms of Example 3, or at least seven primers complementary to at least seven polymorphisms of Example 3, or at least eight primers complementary to at least eight polymorphisms of Example 3, or at least nine primers complementary to at least nine polymorphisms of Example 3, or ten primers complementary to ten polymorphisms of Example 3.

Example 14

The method of any preceding Example, wherein said identification step is carried out using at least two detectable probes complementary to at least two polymorphisms of Example 3, or at least three detectable probes complementary to at least three polymorphisms of Example 3, or at least four detectable probes complementary to at least four polymorphisms of Example 3, or at least five detectable probes complementary to at least five polymorphisms of Example 3, or at least six detectable probes complementary to at least six polymorphisms of Example 3, or at least seven detectable probes complementary to at least seven polymorphisms of claim 3, or at least eight detectable probes complementary to at least eight polymorphisms of Example 3, or at least nine detectable probes complementary to at least nine polymorphisms of Example 3, or ten detectable probes complementary to ten polymorphisms of Example 3.

Example 15

A kit for predicting the odds of lung toxicity in a patient having Hodgkin Lymphoma in response to treatment using bleomycin, comprising a means for determining the presence of one or more polymorphisms of any preceding example, and instructions for recommended treatment of the patient based on the presence of said polymorphisms.

Example 16

The kit of Example 15, wherein the means are selected from a primer according to Example 13 or a detectable probe according to Example 14.

REFERENCES

1. AmericanCancerSociety. Cancer Facts and FIGS. 2015, 2015.
2. Friedman D L, Constine L S. Late effects of treatment for Hodgkin lymphoma. Journal of the National Comprehensive Cancer Network: JNCCN 2006; 4(3): 249-57.
3. Mertens A C, Yasui Y, Liu Y, et al. Pulmonary complications in survivors of childhood and adolescent cancer. A report from the Childhood Cancer Survivor Study. Cancer 2002; 95(11): 2431-41.
4. Martin W G, Ristow K M, Habermann T M, Colgan J P, Witzig T E, Ansell S M. Bleomycin pulmonary toxicity has a negative impact on the outcome of patients with Hodgkin's lymphoma. Journal of clinical oncology: official journal of the American Society of Clinical Oncology 2005; 23(30): 7614-20.
5. Carver J R, Shapiro C L, Ng A, et al. American Society of Clinical Oncology clinical evidence review on the ongoing care of adult cancer survivors: cardiac and pulmonary late effects. Journal of clinical oncology: official journal of the American Society of Clinical Oncology 2007; 25(25): 3991-4008.
6. Schwartz C L, Constine L S, Villaluna D, et al. A risk-adapted, response-based approach using ABVE-PC for children and adolescents with intermediate- and high-risk Hodgkin lymphoma: the results of P9425. Blood 2009; 114(10): 2051-9.
7. Wolden S L, Chen L, Kelly K M, et al. Long-term results of CCG 5942: a randomized comparison of chemotherapy with and without radiotherapy for children with Hodgkin's lymphoma—a report from the Children's Oncology Group. Journal of clinical oncology: official journal of the American Society of Clinical Oncology 2012; 30(26): 3174-80.
8. Kung F H, Schwartz C L, Ferree C R, et al. POG 8625: a randomized trial comparing chemotherapy with chemoradiotherapy for children and adolescents with Stages I, IIA, IIIA1 Hodgkin Disease: a report from the Children's Oncology Group. Journal of pediatric hematology/oncology 2006; 28(6): 362-8.
9. Friedman D L, Chen L, Wolden S, et al. Dose-intensive response-based chemotherapy and radiation therapy for children and adolescents with newly diagnosed intermediate-risk hodgkin lymphoma: a report from the Children's Oncology Group Study AHOD0031. Journal of clinical oncology: official journal of the American Society of Clinical Oncology 2014; 32(32): 3651-8.
10. Wilson J F, Weale M E, Smith A C, et al. Population genetic structure of variable drug response. Nature genetics 2001; 29(3): 265-9.
11. Gupta V H, Amarapurkar D N, Singh M, et al. Association of N-acetyltransferase 2 and cytochrome P450 2E1 gene polymorphisms with antituberculosis drug-induced hepatotoxicity in Western India. Journal of gastroenterology and hepatology 2013; 28(8): 1368-74.
12. Garcia-Closas M, Malats N, Silverman D, et al. NAT2 slow acetylation, GSTM1 null genotype, and risk of bladder cancer: results from the Spanish Bladder Cancer Study and meta-analyses. Lancet 2005; 366(9486): 649-59.
13. Gonzalez C A, Sala N, Capella G. Genetic susceptibility and gastric cancer risk. International journal of cancer Journal international du cancer 2002; 100(3): 249-60.
14. Konig S K, Herzog M, Theile D, Zembruski N, Haefeli W E, Weiss J. Impact of drug transporters on cellular resistance towards saquinavir and darunavir. The Journal of antimicrobial chemotherapy 2010; 65(11): 2319-28.
15. Letourneau I J, Deeley R G, Cole S P. Functional characterization of non-synonymous single nucleotide polymorphisms in the gene encoding human multidrug resistance protein 1 (MRP1/ABCC1). Pharmacogenetics and genomics 2005; 15(9): 647-57.
16. leiri I, Higuchi S, Sugiyama Y. Genetic polymorphisms of uptake (OATP1B1, 1B3) and efflux (MRP2, BCRP) transporters: implications for inter-individual differences in the pharmacokinetics and pharmacodynamics of statins and other clinically relevant drugs. Expert opinion on drug metabolism & toxicology 2009; 5(7): 703-29.
17. Wang H, Jin G, Wang H, et al. Genetic susceptibility of lung cancer associated with common variants in the 3' untranslated regions of the adenosine triphosphate-binding cassette B1 (ABCB1) and ABCC1 candidate transporter genes for carcinogen export. Cancer 2009; 115(3): 595-607.
18. Xu M, Wang Y Z. miR133a suppresses cell proliferation, migration and invasion in human lung cancer by targeting MMP14. Oncology reports 2013; 30(3): 1398-404.
19. Xiong S, Zheng Y, Jiang P, Liu R, Liu X, Chu Y. MicroRNA-7 inhibits the growth of human non-small cell lung cancer A549 cells through targeting BCL-2. International journal of biological sciences 2011; 7(6): 805-14.
20. Tang D, Shen Y, Wang M, et al. Identification of plasma microRNAs as novel noninvasive biomarkers for early detection of lung cancer. European journal of cancer prevention: the official journal of the European Cancer Prevention Organisation 2013; 22(6): 540-8.
21. Cho W C, Chow A S, Au J S. MiR-145 inhibits cell proliferation of human lung adenocarcinoma by targeting EGFR and NUDT1. RNA biology 2011; 8(1): 125-31.
22. Guo J, Feng Z, Huang Z, Wang H, Lu W. MicroRNA-217 functions as a tumour suppressor gene and correlates with cell resistance to cisplatin in lung cancer. Molecules and cells 2014; 37(9): 664-71.
23. Crawford M, Batte K, Yu L, et al. MicroRNA 133B targets pro-survival molecules MCL-1 and BCL2L2 in lung cancer. Biochemical and biophysical research communications 2009; 388(3): 483-9.
24. Lino Cardenas C L, Henaoui I S, Courcot E, et al. miR-199a-5p Is unregulated during fibrogenic response to tissue injury and mediates TGFbeta-induced lung fibroblast activation by targeting caveolin-1. PLoS genetics 2013; 9(2): e1003291.
25. Yang S, Cui H, Xie N, et al. miR-145 regulates myofibroblast differentiation and lung fibrosis. FASEB journal: official publication of the Federation of American Societies for Experimental Biology 2013; 27(6): 2382-91.
26. Liang A, Wang Y, Woodard L E, et al. Loss of glutathione S-transferase A4 accelerates obstruction-induced tubule damage and renal fibrosis. The Journal of pathology 2012; 228(4): 448-58.
27. Hartkoorn R C, Kwan W S, Shallcross V, et al. HIV protease inhibitors are substrates for OATP1A2, OATP1B1 and OATP1B3 and lopinavir plasma concentrations are influenced by SLCO1B1 polymorphisms. Pharmacogenetics and genomics 2010; 20(2): 112-20.
28. Provost P R, Tremblay Y. Genes involved in the adrenal pathway of glucocorticoid synthesis are transiently expressed in the developing lung. Endocrinology 2005; 146(5): 2239-45.
29. Zhang L, Oh S Y, Wu X, et al. SHP-1 deficient mast cells are hyperresponsive to stimulation and critical in initiating allergic inflammation in the lung. Journal of immunology 2010; 184(3): 1180-90.
30. Higa G M, AlKhouri N, Auber M L. Elevation of the erythrocyte sedimentation rate precedes exacerbation of bleomycin-induced pulmonary toxicity: report of two cases and review of literature. Pharmacotherapy 1997; 17(6): 1315-21.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating an individual having a proliferative disorder, comprising the steps of
    a) identifying a polymorphism in one or more genes selected from NAT2, SLCO1B1, ABCC1, GSTA4, SLC7A8, and SLCO3A1, in a biological sample of said individual;
    b) measuring an erythrocyte sedimentation rate (ESR) of said individual;
    c) calculating a log-odds score of said ESR measurement;
    d) determining a bleomycin-associated lung toxicity risk level for said individual based on the presence or absence of said polymorphism in combination with said ESR log-odds score of said individual;
    e) characterizing an individual as high risk for bleomycin-associated lung toxicity or low risk for bleomycin-associated lung toxicity based on said bleomycin-associated lung toxicity risk level; and
    f) administering to the individual characterized as high risk for bleomycin-associated lung toxicity a therapy that does not contain bleomycin or administering to the individual characterized as low risk for bleomycin-associated lung toxicity a therapy that comprises bleomycin.

2. The method of claim 1, wherein said proliferative disorder is cancer.

3. The method of claim 2, wherein said identification step comprises identifying a first allelic risk score based on the identification of the polymorphisms in NAT2, SLCO3A1, and ABCC1.

4. The method of claim 1, wherein said proliferative disorder is a cancer selected from Hodgkin's lymphoma, Non-Hodgkin lymphoma, penile cancer, squamous cell carcinoma of the head and neck, squamous cell carcinoma of the vulva, testicular cancer, ovarian and cervical cancer.

5. The method of claim 1 wherein said polymorphism is a single nucleotide polymorphism selected from rs1799930 in NAT2, rs1041983 in NAT2, rs2291075 in SLCO1B1, rs212091 in ABCC1, rs13197674 in GSTA4, rs4149015 in GSTA4, rs4736312 in CYP11B1, rs2268873 in SLC7A8, rs1517618 in SLCO3A1, or a combination thereof.

6. The method of claim 5, wherein the presence of said polymorphisms in NAT2, SLCO3A1, and ABCC1 is used to generate an allelic risk score ranging from 0 to 5.

7. The method of claim 1, wherein said therapy that does not contain bleomycin is a combination comprising vincristine (Oncovin), etoposide, prednisone, and doxorubicin (Adriamycin), ("OEPA").

8. The method of claim 1, wherein said therapy that does not contain bleomycin is cyclophosphamide, vincristine, prednisone, and dacarbazine (Dac), ("COPDac").

9. The method of claim 1, wherein said biological sample is any biological fluid containing DNA.

10. The method of claim 1, wherein said biological sample is selected from a tissue, a cell, blood, saliva, or a combination thereof.

11. The method of claim 1, wherein said identifying is carried out using a primer complementary to a polymorphism selected from rs2291075 in SLCO1B1, rs212091 in ABCC1, rs13197674 in GSTA4, rs4149015 in GSTA4, rs4736312 in CYP11B1, rs2268873 in SLC7A8, rs1517618 in SLCO3A1, or a combination thereof.

12. The method of claim 1, wherein said identification step is carried out using at least two primers complementary to at least two polymorphisms selected from rs2291075 in SLCO1B1, rs212091 in ABCC1, rs13197674 in GSTA4, rs4149015 in GSTA4, rs4736312 in CYP11JB1, rs2268873 in SLC7A8, rs1517618 in SLCO3A1, or a combination thereof.

13. The method of claim 1, wherein said identification step is carried out using at least two detectable probes complementary to at least two polymorphisms of selected from rs2291075 in SLCO1B1, rs212091 in ABCC1, rs13197674 in GSTA4, rs4149015 in GSTA4, rs4736312 in CYP11JB1, rs2268873 in SLC7A8, rs1517618 in SLCO3A1, or a combination thereof.

14. The method of claim 1, wherein the one or more genes comprises further comprising identifying a polymorphism in NAT2.

15. The method of claim 14, wherein said polymorphism is a single nucleotide polymorphism selected from one or both of rs1799930 in NAT2, and rs1041983 in NAT2.

16. The method of claim 1, wherein said identifying is carried out using one or more primers, said one or more primers being complementary to a polymorphism selected from one or both of rs1799930 in NAT2, and rs1041983 in NAT2.

17. The method of claim 1, further comprising identifying a polymorphism in CYP11B2.

18. The method of claim 17, wherein said polymorphism is rs5305 in CYP11B2.

19. The method of claim 17, wherein said identifying is carried out using a primer complementary to rs5305 in CYP11B2.

* * * * *